United States Patent
Honda et al.

(10) Patent No.: US 8,075,475 B2
(45) Date of Patent: Dec. 13, 2011

(54) ENDOSCOPE SYSTEM AND MEDICAL INSTRUMENT

(75) Inventors: Kazuki Honda, Hachioji (JP); Kazushi Murakami, Hino (JP); Hiroaki Ichikawa, Hachioji (JP); Takehiro Nishiie, Akishima (JP); Yasuhito Kura, Hachioji (JP); Yoshio Onuki, Hachioji (JP); Takaaki Komiya, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 599 days.

(21) Appl. No.: 12/189,897

(22) Filed: Aug. 12, 2008

(65) Prior Publication Data

US 2008/0294003 A1 Nov. 27, 2008

Related U.S. Application Data

(63) Continuation of application No. PCT/JP2006/303075, filed on Feb. 21, 2006.

(51) Int. Cl.
*A61B 1/00* (2006.01)
*A61M 5/178* (2006.01)
(52) U.S. Cl. .................. 600/106; 600/104; 604/159
(58) Field of Classification Search .................. 600/106, 600/102, 104, 114; 604/159, 171
See application file for complete search history.

(56) References Cited

U.S. PATENT DOCUMENTS

| | | | |
|---|---|---|---|
| 2,129,391 A * | 9/1938 | Wappler | 600/104 |
| 3,206,782 A * | 9/1965 | Larsen | 15/104.33 |
| 3,835,854 A * | 9/1974 | Jewett | 604/159 |
| 4,383,532 A * | 5/1983 | Dickhudt | 607/117 |
| 5,201,714 A * | 4/1993 | Gentelia et al. | 604/167.04 |
| 6,078,831 A * | 6/2000 | Belef et al. | 600/424 |
| 6,171,234 B1 * | 1/2001 | White et al. | 600/102 |
| 6,358,199 B1 * | 3/2002 | Pauker et al. | 600/114 |
| 6,428,468 B1 * | 8/2002 | Knighton et al. | 600/36 |
| 7,250,057 B2 * | 7/2007 | Forsberg | 606/213 |
| 7,294,135 B2 * | 11/2007 | Stephens et al. | 606/108 |
| 7,326,236 B2 * | 2/2008 | Andreas et al. | 623/1.11 |
| 2002/0016566 A1 | 2/2002 | Bertolero et al. | |

FOREIGN PATENT DOCUMENTS

| | | |
|---|---|---|
| JP | 57-190541 | 11/1982 |
| JP | 2000-000207 | 1/2000 |
| JP | 2005-073760 | 3/2005 |
| JP | 2005-270171 | 10/2005 |
| WO | WO 97/37716 | 10/1997 |

* cited by examiner

*Primary Examiner* — John P Leubecker
*Assistant Examiner* — Alireza Nia
(74) *Attorney, Agent, or Firm* — Scully, Scott, Murphy & Presser, P.C.

(57) ABSTRACT

According to the present invention, there is provided an endoscope system including: an endoscope having an elongated insertion portion; a medical instrument configured to be inserted in a channel of the insertion portion of the endoscope and to have an elongated flexible sheath; and an advancing and retracting apparatus configured to advance and retract the sheath of the medical instrument in the channel with two rollers, wherein the sheath of the medical instrument is configured to have an outer diameter larger than the distance between the roller surfaces of the two rollers, and to have a frictional resistance increasing unit for increasing frictional resistance between the respective roller surfaces and the outer peripheral surface of the sheath in contact with the respective roller surfaces in a state where the sheath is inserted between the two rollers.

14 Claims, 16 Drawing Sheets

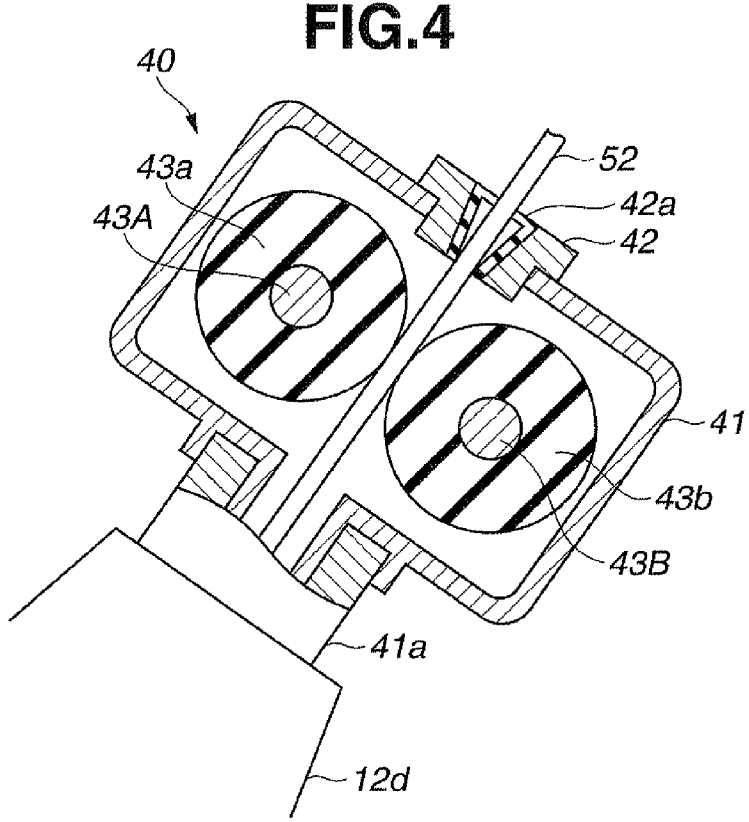
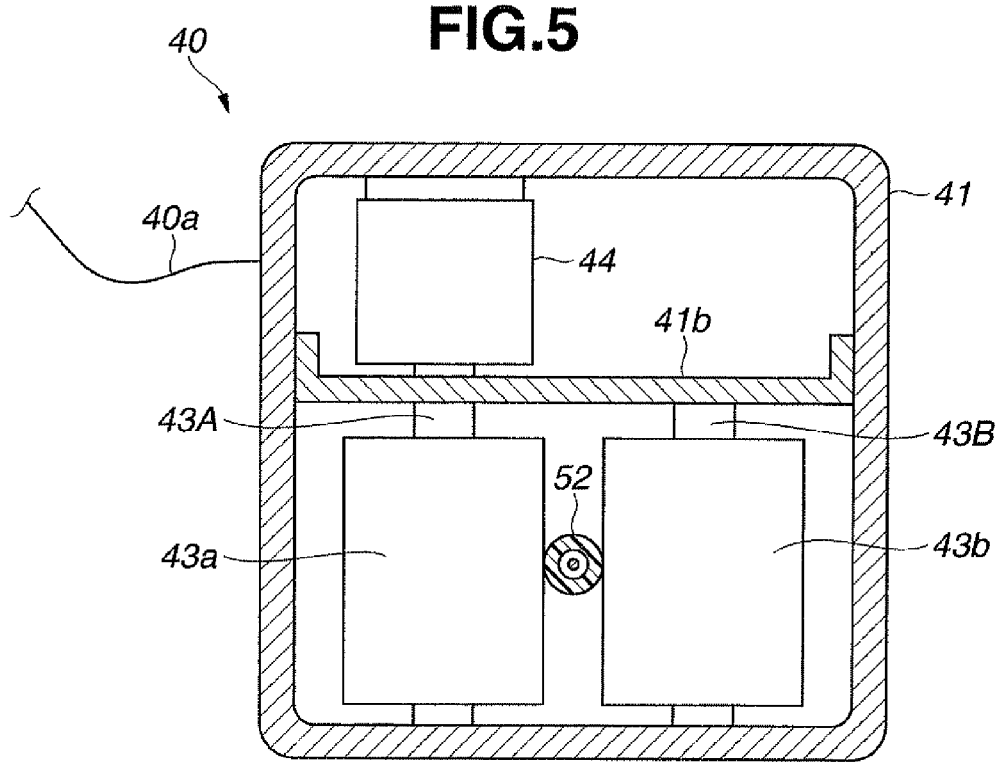

ENDOSCOPE SYSTEM AND MEDICAL INSTRUMENT

CROSS REFERENCE TO RELATED APPLICATION

This application is a continuation application of PCT/JP2006/303075 filed on Feb. 21, 2006, the entire contents of which are incorporated herein by this reference.

BACKGROUND OF THE INVENTION

1. Field of the Invention

The present invention relates to a medical instrument used together with an endoscope and to an endoscope system which facilitates various operations of the medical equipment or functional operations of the endoscope.

2. Description of the Related Art

In recent years, endoscopes have been widely used in the medical field. The endoscope generally includes an elongated insertion portion, a bendable bending portion which is provided at the distal end portion of the insertion portion, and an operation portion in which knobs, switches, and the like, for performing various operations of endoscopic functions are provided.

The endoscope allows the insertion portion to be inserted into the body cavity of a subject so that an organ in a body cavity can be observed or a treatment instrument inserted into a treatment instrument channel can be used to perform various treatment operations, as required.

When the treatment instrument is inserted into the treatment instrument channel in the conventional endoscope used for medical treatment, a surgeon manually introduces the sheath of the treatment instrument into the treatment instrument channel while holding the sheath. However, the insertion performed in this way is cumbersome, and further, the insertion of the treatment instrument as long as 2 m requires attentiveness besides the cumbersomeness. Thus, the insertion and various operations of the treatment instrument are very laborious.

In order to solve the above described problems, for example, in Japanese Patent Application Laid-Open Publication No. 57-190541, there is disclosed an endoscope which includes a treatment instrument inserting and extracting apparatus for inserting and extracting a treatment instrument into and from a treatment instrument channel of the endoscope, and in which, when the treatment instrument reaches the vicinity of the distal end of the insertion portion of the endoscope, the mechanical insertion can be cancelled and a delicate insertion can be manually performed.

Further, in Japanese Patent Application Laid-Open Publication No. 2000-207, there is disclosed an endoscope treatment instrument inserting and extracting apparatus which, in addition to a function of inserting and extracting a treatment instrument into and from a treatment instrument channel of an endoscope, includes treatment instrument operation means for operating a treatment portion provided at the distal end of the treatment instrument, and in which various operations of the treatment instrument inserting and extracting apparatus are performed by means of a foot switch.

The treatment instrument inserting and extracting apparatus or the endoscope treatment instrument inserting and extracting apparatus as disclosed in Japanese Patent Application Laid-Open Publication No. 57-190541 or Japanese Patent Application Laid-Open Publication No. 2000-207 include a metallic spiral pipe sheath which is formed by spirally winding metallic non-stranded wires into a tube, a tubular flexible sheath formed of a synthetic resin or an elastic member, and the like.

In these treatment instrument inserting and extracting apparatuses, a treatment instrument is moved forward and backward by the friction between respective roller surfaces of a drive roller for transmitting the torque of a motor and a freely rotatable driven roller, and the treatment instrument sheath surface which is brought into press contact with the roller surfaces.

SUMMARY OF THE INVENTION

According to the present invention, there is provided an endoscope system including: an endoscope having an elongated insertion portion; a medical instrument having an elongated flexible sheath which is inserted into a channel of the insertion portion of the endoscope; and an advancing and retracting apparatus configured to advance and retract the sheath of the medical instrument in the channel with two rollers, wherein the sheath of the medical instrument is configured to have an outer diameter larger than the distance between the roller surfaces of the two rollers, and to include frictional resistance increasing unit for increasing frictional resistance between the each roller surface and the outer peripheral surface of the sheath, in contact with the each roller surface in a state where the sheath is inserted between the two rollers.

Further, a medical instrument according to the present invention is a medical instrument which is inserted into the channel of the insertion portion of the endoscope, and which is advanced and retracted in the channel by the advancing and retracting apparatus having two rollers, the medical instrument including: a treatment portion which is led out from the distal end of the insertion portion and which is used to perform various treatment operations in a body cavity; and an elongated flexible sheath to the distal end side of which the treatment portion is continuously connected, wherein the sheath has an outer diameter larger than a distance between the roller surfaces of the two rollers and includes frictional resistance increasing unit for increasing frictional resistance between the each roller surface and the outer peripheral surface of the sheath, in contact with the each roller surface in a state where the sheath is inserted between the two rollers.

According to the present invention, it is possible to realize an endoscope system and a medical instrument, which enable a treatment instrument sheath of a treatment instrument to be smoothly advanced and retracted.

BRIEF DESCRIPTION OF THE DRAWINGS

FIG. 4 is a longitudinal sectional view showing an internal configuration of a motor-driven treatment instrument advance/retract apparatus, according to the first embodiment;

FIG. 5 is a lateral sectional view showing the internal configuration of the motor-driven treatment instrument advance/retract apparatus, according to the first embodiment;

DETAILED DESCRIPTION OF THE PREFERRED EMBODIMENT(S)

In the following, embodiments of an endoscope system and a medical instrument according to the present invention will be described with reference to the accompanying drawings.

First Embodiment

Figure 1:
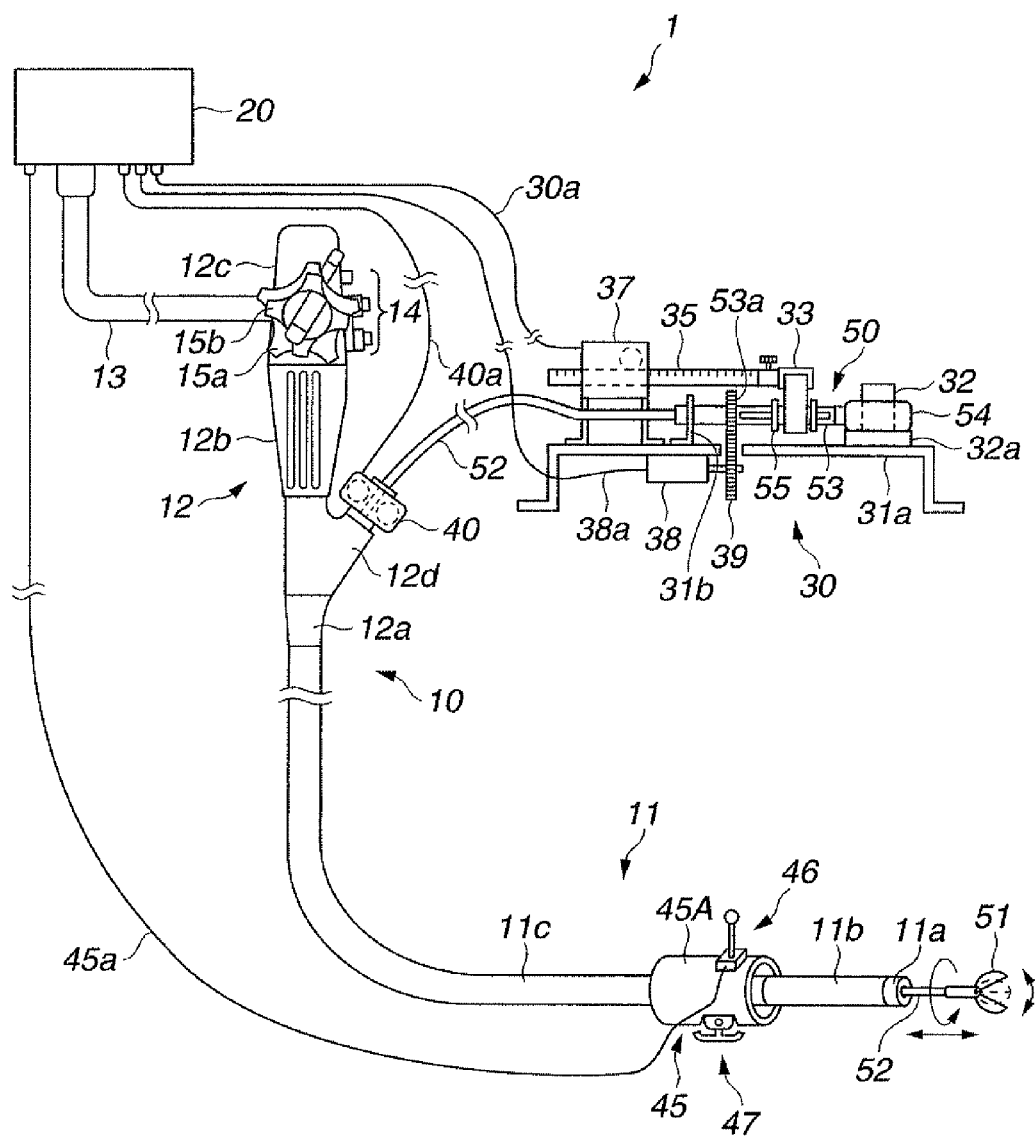
FIG. 1 is a view showing an entire configuration of an endoscope system according to a first embodiment.
Figure 2:
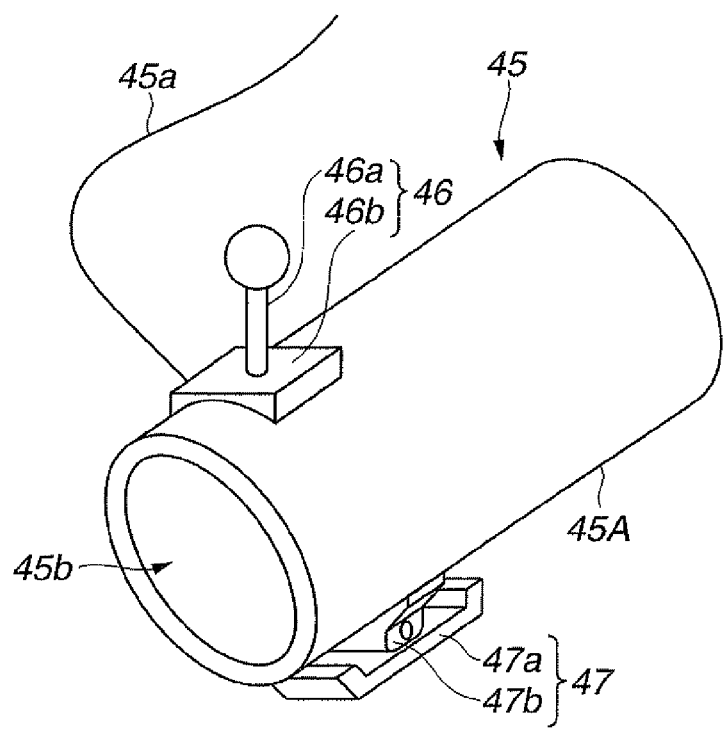
FIG. 2 is a view showing an operation instruction apparatus of the endoscope system, according to the first embodiment.
Figure 3:
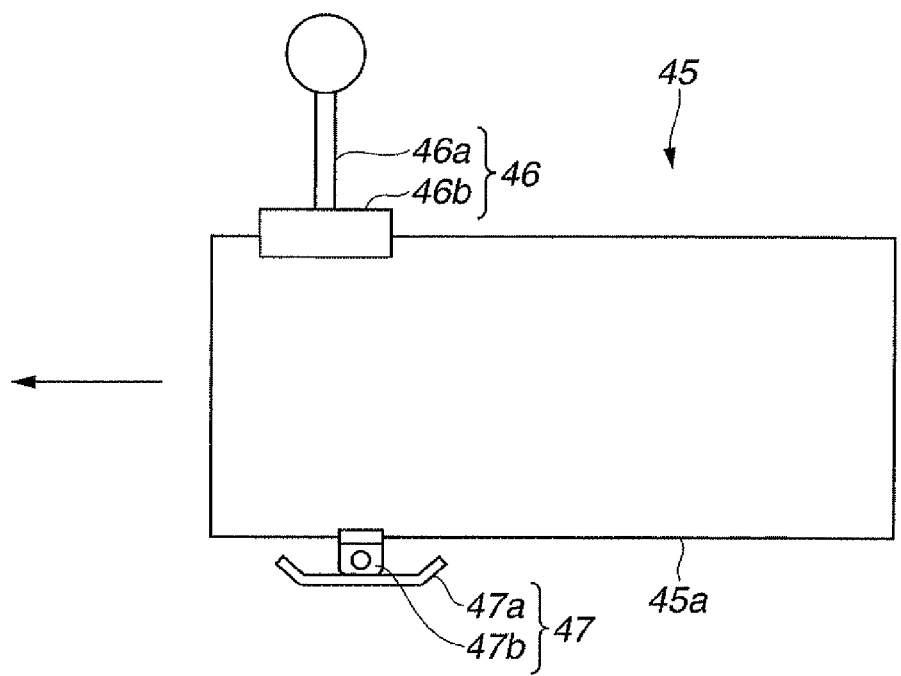
FIG. 3 is a plan view when the operation instruction apparatus is seen from the side, according to the first embodiment.
Figure 6:
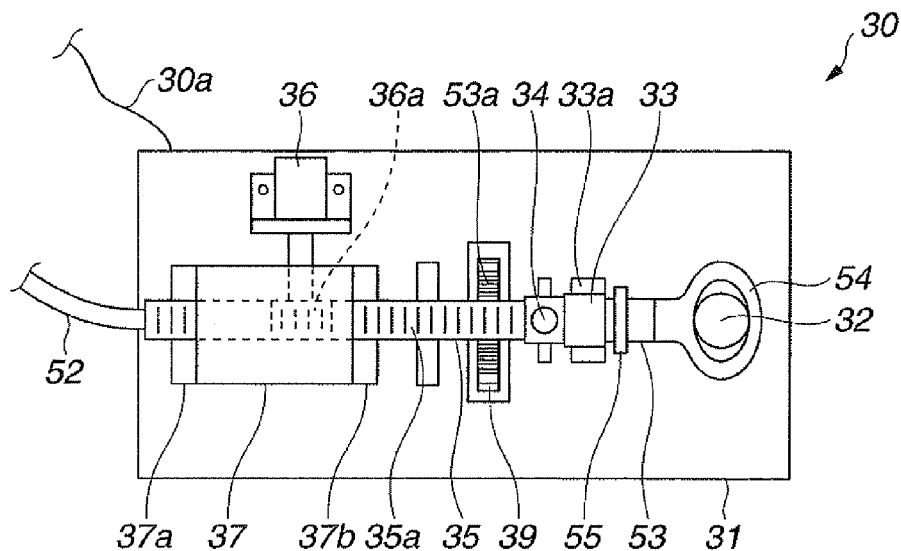
FIG. 6 is a plan view when a motor-driven treatment instrument open/close apparatus is seen from the above, according to the first embodiment.
Figure 7:
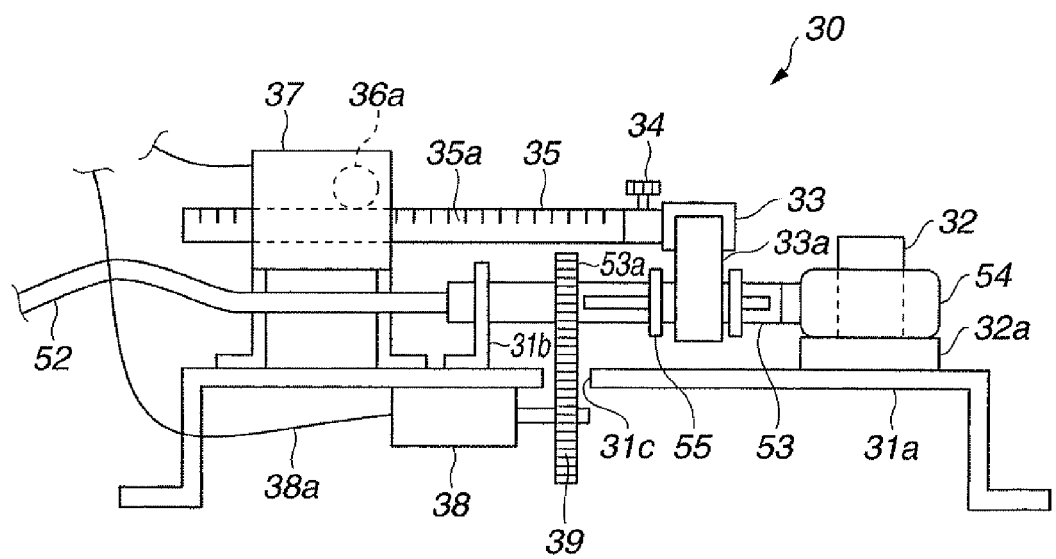
FIG. 7 is a plan view when the motor-driven treatment instrument open/close apparatus is seen from the side, according to the first embodiment.
Figure 8:
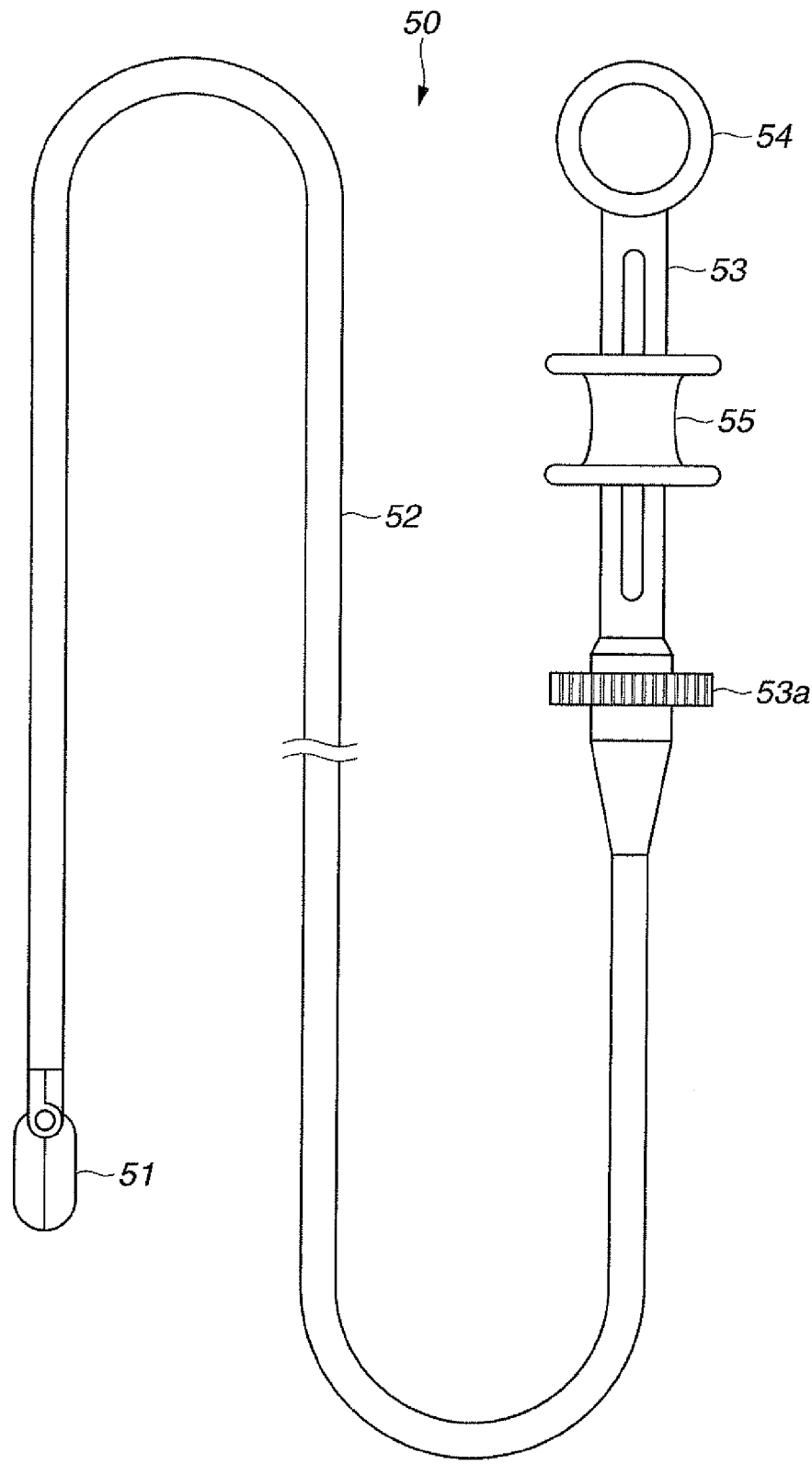
FIG. 8 is a view showing an entire configuration of a treatment instrument, according to the first embodiment.
Figure 9:
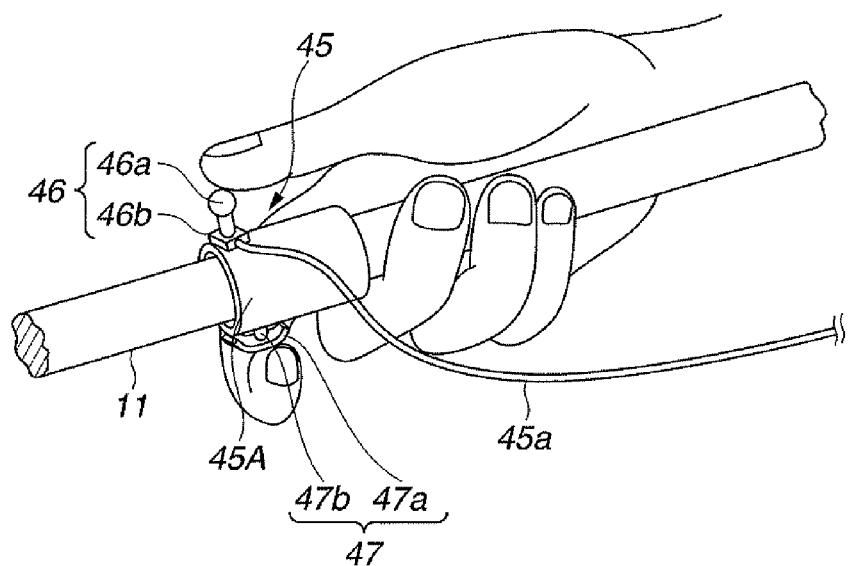
FIG. 9 is a view showing a state where the operation instruction apparatus is mounted to an insertion portion of an endoscope, according to the first embodiment.
Figure 10:
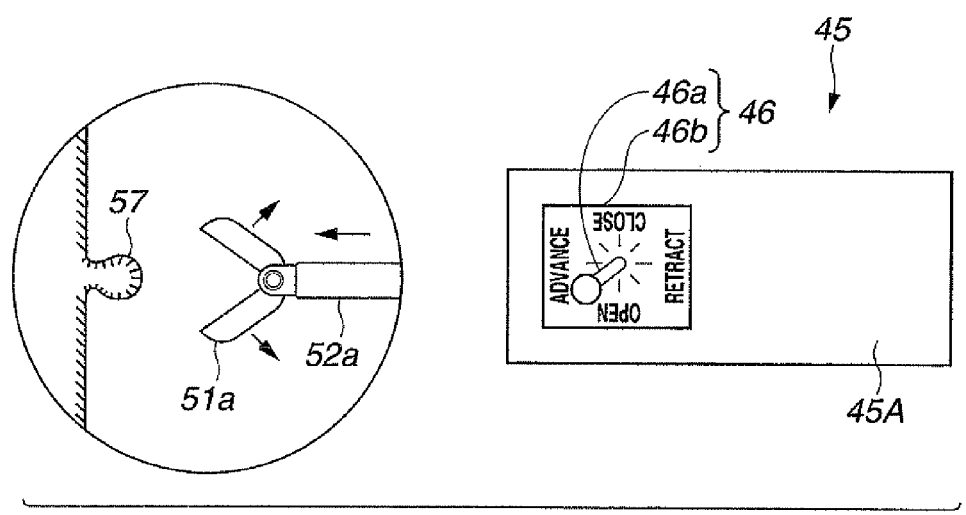
FIG. 10 is a view for explaining an example of an advance/retract and open/close operation of the treatment instrument by the operation instruction apparatus, according to the first embodiment.
Figure 11:
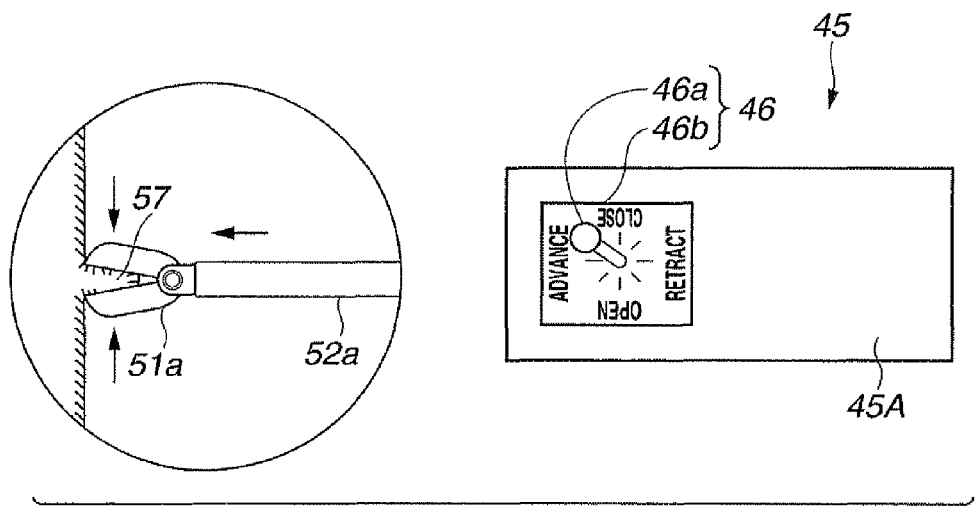
FIG. 11 is a view for explaining an example of the advance/retract and open/close operation of the treatment instrument by the operation instruction apparatus, according to the first embodiment.
Figure 12:
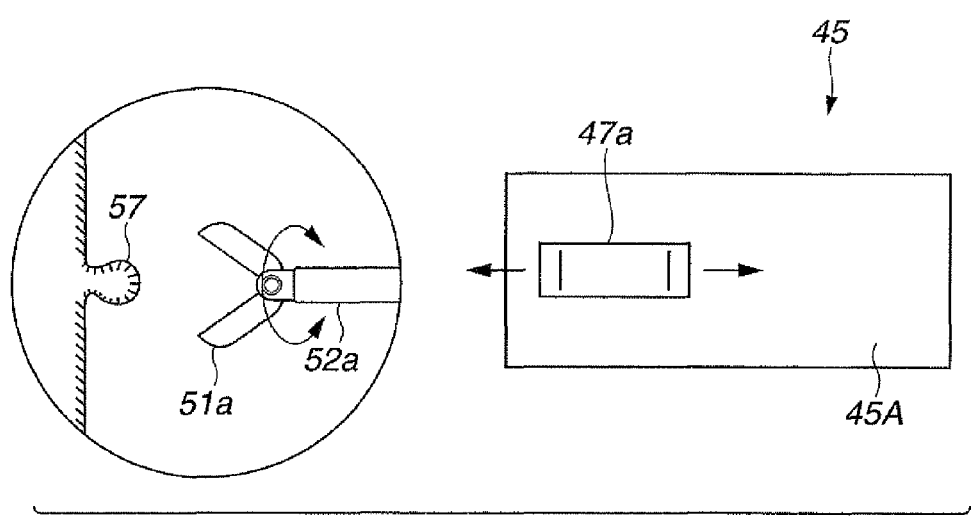
FIG. 12 is a view for explaining an example of a rotation operation of the treatment portion of the treatment instrument by the operation instruction apparatus, according to the first embodiment.
Figure 13:
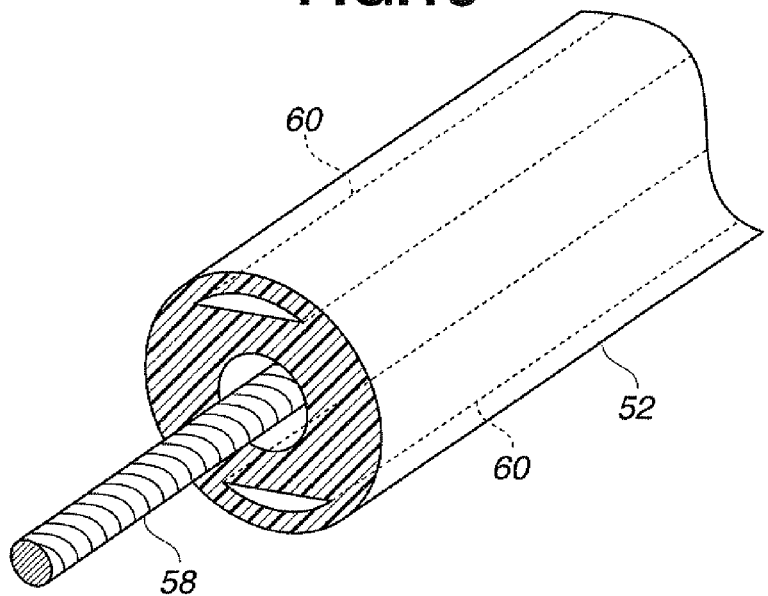
FIG. 13 is a perspective view showing, partially in cross section, a sheath of the treatment instrument, according to the first embodiment.
Figure 14:
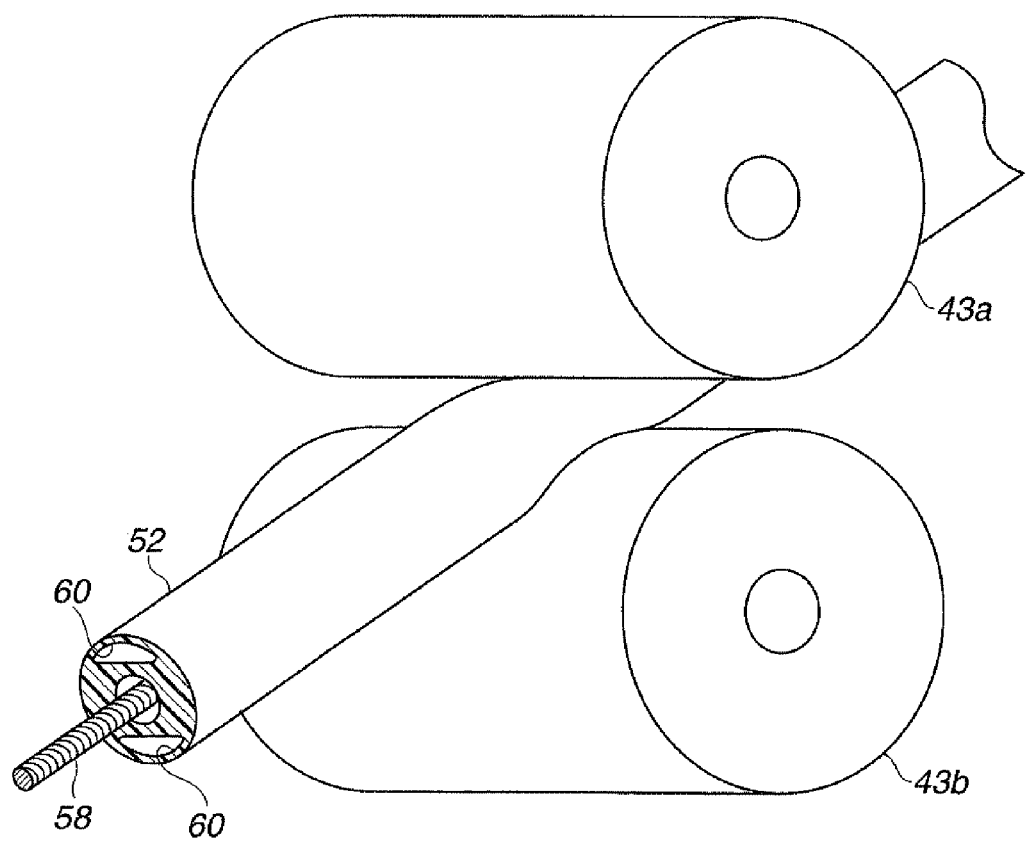
FIG. 14 is a perspective view showing the sheath in a state where the sheath is inserted between respective rollers of the motor-driven treatment instrument advance/retract apparatus, according to the first embodiment.
Figure 15:
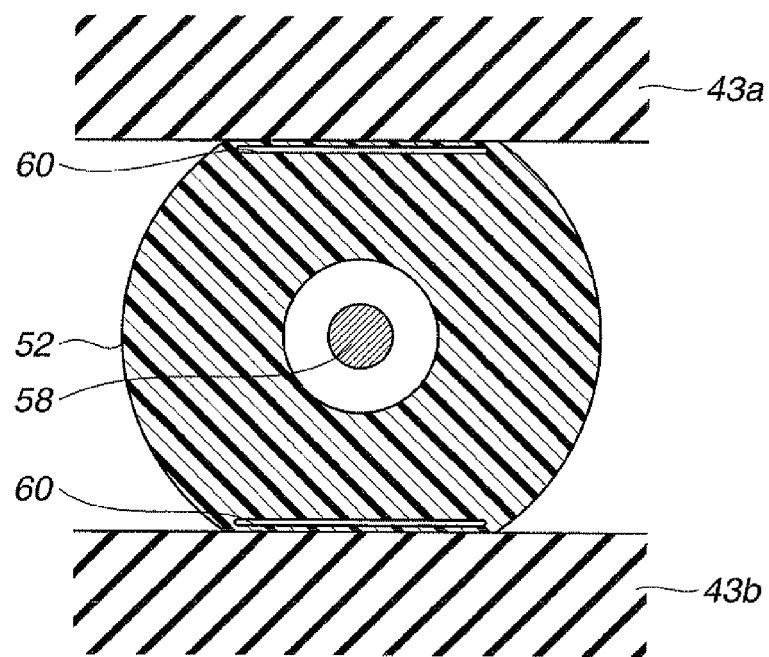
FIG. 15 is a sectional view showing the sheath in the state where the sheath is inserted between the respective rollers of the motor-driven treatment instrument advance/retract apparatus, according to the first embodiment.
Figure 16:
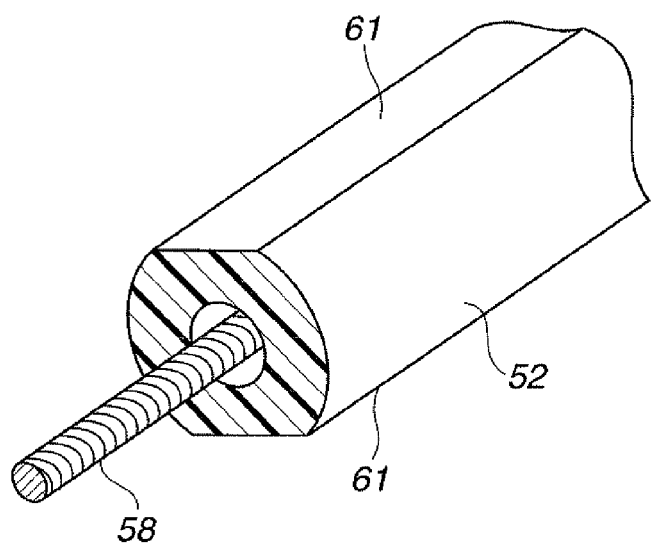
FIG. 16 is a perspective view showing, partially in cross section, a treatment instrument sheath of a first modification, according to the first embodiment.
Figure 17:
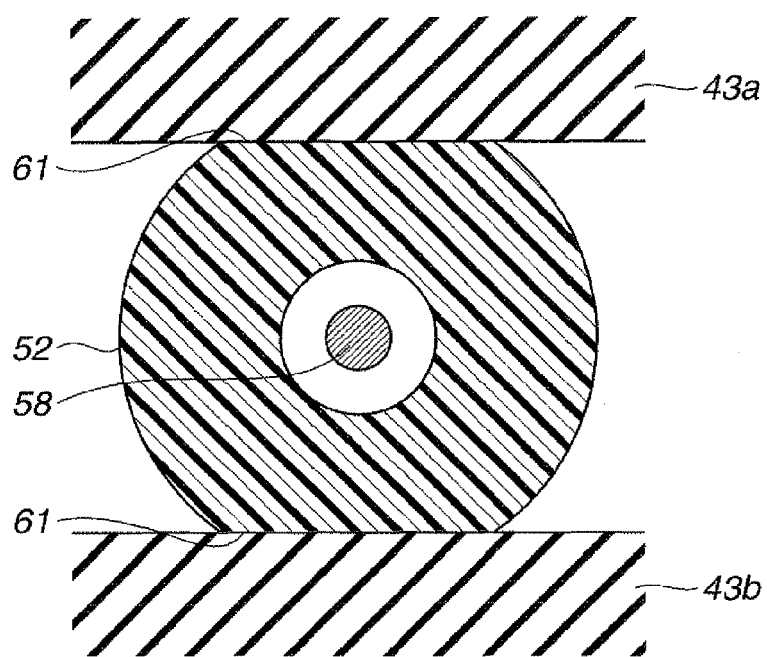
FIG. 17 is a sectional view showing the sheath in a state where the sheath of the first modification is inserted between respective rollers of the motor-driven treatment instrument advance/retract apparatus, according to the first embodiment.
Figure 18:
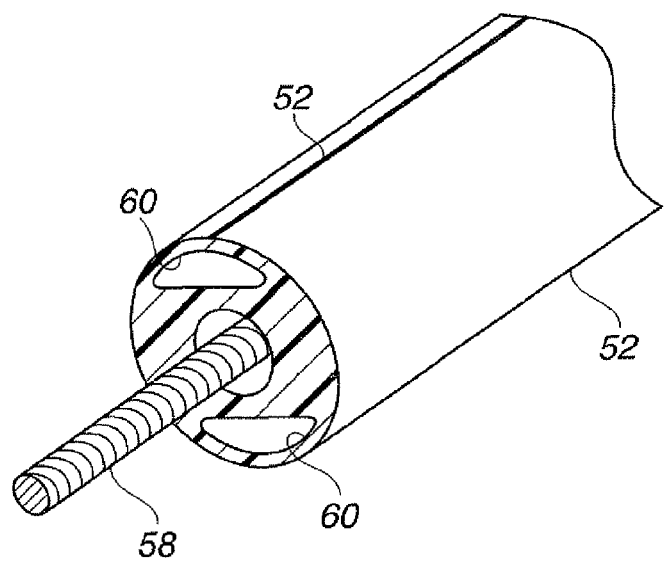
FIG. 18 is a perspective view showing a second modification and showing, partially in cross section, a treatment instrument sheath having a first index portion, according to the first embodiment.
Figure 19:
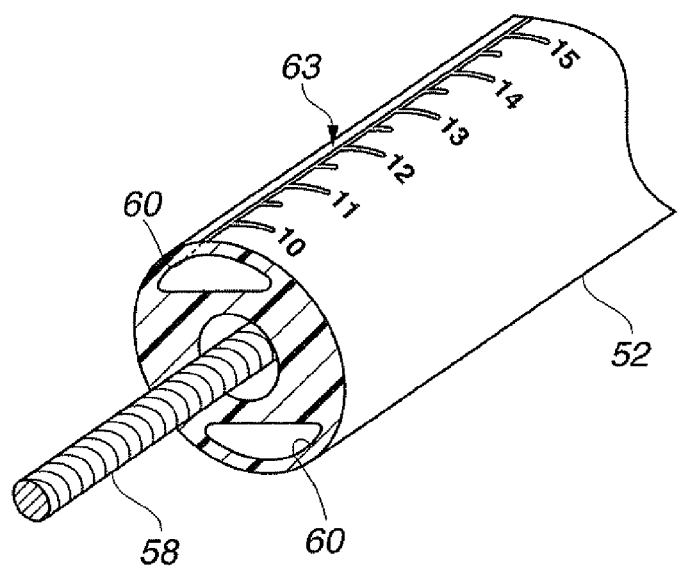
FIG. 19 is a perspective view showing a third modification and showing, partially in cross section, a treatment instrument sheath having a second index portion, according to the first embodiment.
Figure 20:
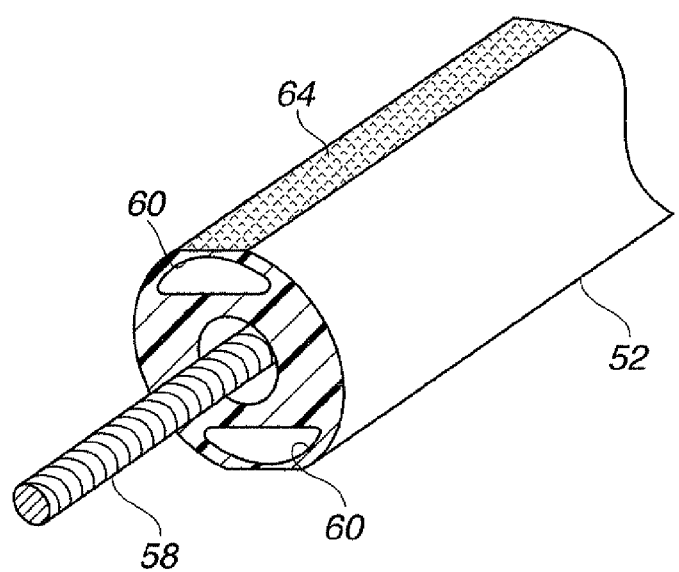
FIG. 20 is a perspective view showing a fourth modification and showing, partially in cross section, a treatment instrument sheath having a third index portion, according to the first embodiment.

First, a first embodiment according to the present invention will be described with reference to FIG. 1 to FIG. 20. Note that FIG. 1 to FIG. 20 relate to the first embodiment according to the present invention. FIG. 1 is a view showing an entire configuration of an endoscope system. FIG. 2 is a view showing an operation instruction apparatus. FIG. 3 is a plan view when the operation instruction apparatus is seen from the side. FIG. 4 is a longitudinal sectional view showing an internal configuration of a motor-driven treatment instrument advance/retract apparatus. FIG. 5 is a lateral sectional view showing the internal configuration of the motor-driven treatment instrument advance/retract apparatus. FIG. 6 is a plan view when a motor-driven treatment instrument open/close apparatus is seen from the above. FIG. 7 is a plan view when the motor-driven treatment instrument open/close apparatus is seen from the side. FIG. 8 is a view showing an entire configuration of a treatment instrument. FIG. 9 is a view showing a state where the operation instruction apparatus is mounted to an insertion portion of an endoscope. FIG. 10 to FIG. 12 are views for explaining examples of operation of the treatment instrument by the operation instruction apparatus. FIG. 13 is a perspective view showing, partially in cross section, a treatment instrument sheath. FIG. 14 is a perspective view showing the sheath in a state where the sheath is inserted between rollers. FIG. 15 is a sectional view showing the sheath in the state where the sheath is inserted between the rollers. FIG. 16 is a perspective view showing, partially in cross section, a treatment instrument sheath of a first modification. FIG. 17 is a sectional view showing the sheath of the first modification in a state where the sheath is inserted between the rollers. FIG. 18 is a perspective view showing a second modification and showing, partially in cross section, a treatment instrument sheath having a first index portion. FIG. 19 is a perspective view showing a third modification and showing, partially in cross section, a treatment instrument sheath having a second index portion. FIG. 20 is a perspective view showing a fourth modification and showing, partially in cross section, a treatment instrument sheath having a third index portion.

As shown in FIG. 1, an endoscope system 1 according to the present embodiment includes an endoscope 10, a control apparatus 20 serving as a light source apparatus and a video processor, a motor-driven treatment instrument open/close apparatus 30, a motor-driven treatment instrument advance/retract apparatus 40, and an operation instruction apparatus 45. Note that in the present embodiment, an endoscope operation assisting apparatus according to the present invention is configured by the control apparatus 20, the motor-driven treatment instrument open/close apparatus 30, the motor-driven treatment instrument advance/retract apparatus 40, and the operation instruction apparatus 45. Note that although not shown, display means, such as a monitor for displaying an endoscopic image, is connected to the control apparatus 20.

The endoscope 10 includes an insertion portion 11, an operation portion 12 which is connected to the proximal end of the insertion portion 11, and a universal cord 13 which is extended from the operation portion 12 and is connected to the control apparatus 20.

The insertion portion 11 is a flexible tube body formed in such a way that a distal end portion 11a, a bending portion 11b, and a flexible tube portion 11c are successively connected in order from the distal end. The operation portion 12 is configured by including, in order from the distal end, a bending prevention portion 12a connected to the proximal end of the flexible tube portion 11c, a grasping portion 12b having a treatment instrument insertion portion 12d, a main operation portion 12c provided with bending knobs 15a and 15b, and with a plurality of switches 14 for performing air supply and water supply operations and suction operation, and for performing operations of various optical systems, such as image pickup means and illumination means which are provided in the distal end portion 11a.

The endoscope 10 includes a treatment instrument channel (not shown) running from the treatment instrument insertion portion 12d to the distal end portion 11a.

The motor-driven treatment instrument open/close apparatus 30 is electrically connected to the control apparatus 20 by an electrical cable 30a, and is provided with a handle portion 53 of a treatment instrument 50 which is a medical instrument, such as a biopsy forceps.

Further, the motor-driven treatment instrument advance/retract apparatus 40 is electrically connected with the control apparatus 20 by an electrical cable 40a and is provided at the treatment instrument insertion portion 12d of the endoscope 10. In the motor-driven treatment instrument advance/retract apparatus 40, a sheath 52 of the treatment instrument 50 is inserted so as to be led into the treatment instrument channel.

The operation instruction apparatus 45 is electrically connected with the control apparatus 20 by a signal cable 45a, and is externally inserted onto the insertion portion 11 of the endoscope 10.

Note that a treatment portion 51 which is here a tissue collecting portion of a biopsy forceps is provided at the distal end of the sheath 52 of the treatment instrument 50. The sheath 52 of the treatment instrument 50 is inserted into the treatment instrument channel via the motor-driven treatment instrument advance/retract apparatus 40 in a state of being freely advanced or retracted so that the treatment portion 51 is led out from the opening of the treatment instrument channel in the distal end portion 11a of the insertion portion 11 or is led into the insertion portion 11.

Next, the operation instruction apparatus 45 will be described in detail with reference to FIG. 2 and FIG. 3.

As shown in FIG. 2, the operation instruction apparatus 45 has an insertion-portion outer insertion tube 45A as a substantially cylindrical insertion portion insertion body having an insertion portion insertion hole 45b. An operation instruction portion 46 configured by an operation lever 46a and an operation lever supporting portion 46b is provided on the outer peripheral surface on the distal end side of the insertion-portion outer insertion tube 45A. The above described signal cable 45a is extended from the operation lever supporting portion 46b of the operation instruction portion 46. Further, in the operation instruction apparatus 45 according to the present embodiment, a rotation instruction portion 47 is provided on the outer peripheral portion opposite to the side where the operation instruction portion 46 is provided. The rotation instruction portion 47 is electrically connected with the signal cable 45a which is extended from the operation instruction portion 46 and connected with the control apparatus 20.

The rotation instruction portion 47 is configured by a rotation operation lever 47a which is rotationally operated about the rotation axis perpendicular to the axial direction of the operation instruction apparatus 45, and an operation lever supporting portion 47b which rotatably holds the rotation operation lever 47a.

Note that the distal end side of the insertion-portion outer insertion tube 45A of the operation instruction apparatus 45 is in the direction of the arrow shown in FIG. 3 and the direction in which the insertion portion 11 is inserted into the body cavity. Thus, the operation instruction apparatus 45 is externally inserted onto the insertion portion 11 in the state as shown in FIG. 1, in such a way that the insertion portion 11 is inserted from the opening of the insertion portion insertion hole 45b on the proximal end side of the insertion-portion outer insertion tube 45A. Further, the insertion portion insertion hole 45b is set to have a hole diameter larger than the outer diameter of the insertion portion 11, and is made to freely slide with respect to the insertion portion 11 in its long axis direction in the state where the insertion portion 11 is loosely inserted into the operation instruction apparatus 45.

Next, the motor-driven treatment instrument advance/retract apparatus 40 will be described in detail with reference to FIG. 4 and FIG. 5.

As shown in FIG. 4 and FIG. 5, in the motor-driven treatment instrument advance/retract apparatus 40, two rollers 43a and 43b are rotatably provided in the inside of a box body 41. On one surface of the box body 41, there is provided a treatment instrument insertion portion 42 into which the sheath 52 of the treatment instrument 50 is inserted. On the side opposite to the one surface, there is provided a scope fixing portion 41a which leads the sheath 52 to the treatment instrument channel of the endoscope 10 and is connected with the treatment instrument insertion portion 12d of the endoscope 10.

In the treatment instrument insertion portion 42, a forceps plug 42a formed of an elastic member is provided in a through hole portion into which the sheath 52 is inserted. Further, the scope fixing portion 41a is sealingly connected to the channel opening portion of the treatment instrument insertion portion 12d of the endoscope 10. Therefore, the motor-driven treatment instrument advance/retract apparatus 40 is configured such that the sealing of the treatment instrument channel is maintained by the forceps plug 42a and the scope fixing portion 41a so as to prevent the pressure in the body cavity from being lowered even at the time when the sheath 52 of the treatment instrument 50 is inserted or extracted in the state where the body cavity is expanded by supplying air or water into the body cavity by the endoscope 10 so as to make the inside of the body cavity easily observed.

The two rollers 43a and 43b provided in the box body 41 are formed of an elastic member, or the like, and are made to freely rotate about the respective rotation axes 43A and 43B. The sheath 52 of the treatment instrument 50 is advanced and retracted in the treatment instrument channel in such a way that the outer surface of the sheath 52 is pressed by the respective rotating roller surfaces.

The roller 43a is a drive side roller, and the rotation axis 43A is driven by a motor 44 provided in the box body 41. On the other hand, the roller 43b is a driven side roller and enables the sheath 52, which is advanced and retracted by the rotation of the drive side roller 43a, to be smoothly advanced and retracted.

Note that the respective rollers 43a and 43b are rotatably supported by the side walls of the box body 41 and a supporting plate body 41b in such a manner that the respective roller surfaces are separated from each other at a predetermined distance and that the respective rotation axes 43A and 43B are in parallel with each other.

Next, the motor-driven treatment instrument open/close apparatus 30 will be described in detail with reference to FIG. 6 and FIG. 7.

As shown in FIGS. 6 and 7, the motor-driven treatment instrument open/close apparatus 30 is configured by including: a plate shaped base body 31; a ring pressing portion 32 projectingly provided on one surface of the base body 31; a slider pressing portion 33 for pinching a slider 55 of the treatment instrument 50; a rack 35 connected to the slider pressing portion 33; a motor 36 having a motor shaft to which a pinion gear 36a meshing with a linear tooth 35a of the rack 35 is attached; a holding box 37 which is fixed to the base body 31 by fixing members 37a and 37b so as to house the pinion gear 36a of the motor 36 and which holds the rack 35 in a linearly advancing and retracting manner; and a holding portion 31b which has a substantially hat-shape section and is arranged on the one surface of the base body 31, and to which the handle portion 53 of the treatment instrument 50 is fixed.

An annular ring base 32a is fitted to the end of the ring pressing portion 32 on the side of the base body 31. A portion of the ring pressing portion 32 projecting from the ring base 32a is inserted into a finger hook ring 54 of the treatment instrument 50 so that the handle portion 53 is fixed to the motor-driven treatment instrument open/close apparatus 30. The ring pressing portion 32 has an outer diameter set to be substantially equal to the inner diameter of the finger hook ring 54, so as to thereby surely hold the handle portion 53 of the treatment instrument 50. Note that the handle portion 53 of the treatment instrument 50 may be surely held in such a way that the outer diameter of the ring pressing portion 32 is set to be slightly smaller than the inner diameter of the finger hook ring 54 and that an elastic tube is made to cover the outer circumference of the ring pressing portion 32.

Further, the ring base 32a is a member which separates the handle portion 53 of the treatment instrument 50 from the base body 31 at a predetermined distance by making the finger hook ring 54 brought into contact with the end surface of the ring base 32a on the side opposite to the base body 31.

The slider pressing portion 33 pinches the slider 55 by two holding plates 33a extended to the lower side when seen toward the paper surface of FIG. 7, that is, to the side of the base body 31. The slider 55 of the treatment instrument 50 is formed into a drum shape which has flanges on both sides thereof. Therefore, the two holding plates 33a hold the slider 55 so as to sandwich the barrel portion between the flanges of the slider 55. As described above, the slider pressing portion 33 is connected to the one end portion of the rack 35 by a set screw 34.

The rack 35 is advanced and retracted together with the slider pressing portion 33 relatively to the holding box 37 by the rotation of the pinion gear 36a of the motor 36, which pinion gear is in mesh with the linear tooth 35a. Thereby, the slider pressing portion 33 holding the slider 55 of the treatment instrument 50 advances and retracts the slider 55 along the axis of the handle portion 53.

Further, the endoscope system 1 according to the present embodiment is configured so as to correspond to the treatment instrument 50 which is a medical instrument, such as a biopsy forceps, having the treatment portion 51 which is freely rotatable together with the sheath 52 about the long axis of the sheath 52. Therefore, in the motor-driven treatment instrument open/close apparatus 30, there is provided a rotating motor 38 for rotating the sheath 52 and the treatment portion 51 about the long axis of the sheath 52 from the distal end portion of the handle portion 53 of the treatment instrument 50.

The rotating motor 38 has a rotation transmission gear (hereinafter simply referred to as gear) 39, which is a spur gear, at the end of the motor shaft, and is electrically connected to the control apparatus 20 by an electrical cable 38a. The rotating motor 38 is fixed to the rear surface side of the base body 31, which is formed to have the substantially hat-shaped section, of the motor-driven treatment instrument open/close apparatus 30 as shown in FIG. 7.

Further, a hole 31c is formed in the base body 31 so that the gear 39 of the rotating motor 38 can be exposed from the surface on the side on which the treatment instrument 50 is arranged. Further, the holding portion 31b which rotatably holds the distal end portion of the handle portion 53 of the treatment instrument 50 is provided on the base body 31.

Further, as shown in FIG. 8, in the treatment instrument 50 according to the present embodiment, there is provided, in the distal end portion of the handle portion 53, a driven gear (hereinafter simply referred to as gear) 53a which is in mesh with the gear 39 exposed from the hole 31c of the base body 31. Further, the sheath 52 of the treatment instrument 50 is a tube formed of synthetic resin, such as for example, nylon, polytetrafluoroethylene resin (PTFE), and polyurethane.

Note that there is inserted into the sheath 52 of the treatment instrument 50 an operation wire (not shown here) whose one end is connected to the treatment portion 51 at the distal end, and whose other end is connected to the slider 55. The operation wire is pulled and slackened according to the advancement and retraction of the slider 55, so as to perform a predetermined operation of the treatment portion 51, that is, to open and close the tissue collecting portion because the treatment portion 51 is here a biopsy forceps.

In the endoscope system 1 configured as described above, first, the operation instruction apparatus 45 is mounted so as to be externally inserted onto the insertion portion 11 as shown in FIG. 9, and the insertion portion 11 of the endoscope 10 is inserted into the body cavity of the subject. The surgeon examines the inside of the body cavity while observing the endoscopic image. For example, when finding out a lesion, the surgeon performs treatment such as excision of the lesion, and the like. Note that in the present embodiment, there will be described an example in the case where the biopsy forceps is used.

First, as described above, the surgeon mounts the operation instruction apparatus 45 to the insertion portion 11 of the endoscope 10 and fixes the handle portion 53 of the treatment instrument 50 to the motor-driven treatment instrument open/close apparatus 30. More particularly, the surgeon mounts the slider pressing portion 33 removed from the rack 35 to the slider 55 of the treatment instrument 50 and inserts the ring pressing portion 32 into the finger hook ring 54 of the handle portion 53.

At this time, the surgeon mounts a part of the handle portion 53 of the treatment instrument 50 to the holding portion 31b provided on the base body 31 and inserts the ring pressing portion 32 into the finger hook ring 54. Then, as shown in FIG. 6 and FIG. 7, the surgeon connects the slider pressing portion 33 to the rack 35 with the set screw 34.

Next, the surgeon mounts the motor-driven treatment instrument advance/retract apparatus 40 to the treatment instrument insertion portion 12d of the endoscope 10 and inserts the sheath 52 from the side of the treatment portion 51 of the treatment instrument 50 into the treatment instrument channel of the endoscope 10 through the motor-driven treatment instrument advance/retract apparatus 40. At this time, the surgeon inserts the sheath 52 until the treatment portion 51 of the treatment instrument 50 is passed through the two rollers 43a and 43b in the motor-driven treatment instrument advance/retract apparatus 40 and the sheath 52 is pressed between the two rollers 43a and 43b. Note that the surgeon may manually send the sheath 52 of the treatment instrument 50 into the treatment instrument channel of the endoscope 10 until the treatment portion 51 of the treatment instrument 50 is positioned at the distal end portion of the insertion portion 11 of the endoscope 10.

Then, the surgeon inserts the insertion portion 11 into the body cavity of the subject, while observing an endoscopic image from the side of the distal end portion 11a. For example, when finding out a lesion in the body cavity, the surgeon grips the insertion portion 11 with one hand to hold the distal end portion 11a of the insertion portion 11 in the body cavity so that the lesion is displayed in the visual field range of the endoscope 10, and holds the operation instruction apparatus 45 with the one hand. At this time, for example, the surgeon holds the operation instruction apparatus 45 in such a manner that the outer peripheral portion of the operation instruction apparatus 45 is pressed so as to be surrounded by the index finger as shown in FIG. 9, and also the surgeon grasps the insertion portion 11 by using the middle finger, the ring finger, and the little finger in such a manner that the thumb is applied to the operation lever 46a and the index finger is applied to the rotation operation lever 47a.

Then, the surgeon performs treatment of the lesion, such as a polyp, in the body cavity, while observing the endoscopic image. More particularly, by tilting the operation lever 46a of the operation instruction portion 46 in the predetermined direction as shown in FIG. 10, the surgeon is capable of making the operation instruction apparatus 45, which is held by the one hand of the surgeon together with the insertion portion 11, perform the opening and closing operation of the treatment portion 51 of the treatment instrument 50 and an advancing and retracting operation of the sheath 52.

In the present embodiment, indexes are arranged on the upper surface of the operation lever supporting portion 46b of the operation instruction portion 46. For example, when the surgeon tilts the operation lever 46a in the distal end direction of the operation instruction portion 46 (the direction of the index "Advance" of the operation lever supporting portion 46b in FIG. 10), that is, the insertion direction along the axis of the insertion portion 11, the surgeon is capable of advancing the sheath 52 of the treatment instrument 50. On the contrary, when the surgeon tilts the operation lever 46a in the proximal end direction of the operation instruction portion 46 (the direction of the index "Retract" of the operation lever supporting portion 46b in FIG. 10), the surgeon is capable of retracting the sheath 52 of the treatment instrument 50.

Further, when the surgeon tilts the operation lever 46a in the direction to the left side (the direction of the index "Open" on the lower side in FIG. 10) which is perpendicular to the axial direction of the operation instruction portion 46, the surgeon is capable of performing the opening operation of the treatment portion of the treatment instrument 50. When the surgeon tilts the operation lever 46a to the right side opposite to the left side (the direction of the index "Close" on the upper side in FIG. 10), the surgeon is capable of performing the closing operation of the treatment portion of the treatment instrument 50.

That is, when the operation lever 46a of the operation instruction portion 46 is tilted in the forward or backward direction (the direction of the index "Advance" or "Retract") of the operation instruction portion 46, the corresponding instruction signal is supplied to the control apparatus 20 (see FIG. 1) via the signal cable 45a. When receiving the instruction signal, the control apparatus 20 supplies electric power to the motor-driven treatment instrument advance/retract apparatus 40 via the electrical cable 40a, and rotates the motor 44 (see FIG. 7) in the motor-driven treatment instrument advance/retract apparatus 40 in the predetermined direction. Then, according to the direction of rotation of the drive side roller 43a rotated by the motor 44 in the motor-driven treatment instrument advance/retract apparatus 40, the sheath 52 of the treatment instrument 50 held between the two rollers 43a and 43b, is advanced or retracted in the treatment instrument channel of the endoscope 10.

As a result, the surgeon is capable of leading the treatment portion 51 of the treatment instrument 50 into or out of the distal end portion 11a of the insertion portion 11 of the endoscope 10 by performing the forward or backward tilting operation of the operation lever 46a of the operation instruction portion 46.

Further, when the operation lever 46a of the operation instruction portion 46 is tilted in the right or left direction (the direction of the index "Open" or "Close") of the operation instruction portion 46, the corresponding instruction signal is supplied to the control apparatus 20 via the signal cable 45a. When receiving the instruction signal, the control apparatus 20 supplies electric power to the motor-driven treatment instrument open/close apparatus 30 via the electrical cable 30a, and rotates the motor 36 of the motor-driven treatment instrument open/close apparatus 30 in the predetermined direction.

Then, according to the direction of rotation of the pinion gear 36a rotated by the motor 36, the rack 35 is linearly moved forward or backward relative to the holding box 37 by the linear tooth 35a which is in mesh with the pinion gear 36a. Thus, the slider pressing portion 33 connected with the rack 35 moves the slider 55 of the treatment instrument 50, which slider is held by the slider pressing portion 33, forward or backward along the axis of the handle portion 53, and thereby pulls and slackens the operation wire of the treatment instrument 50.

As a result, the surgeon is capable of performing the opening or closing operation of the treatment portion 51 of the treatment instrument 50 by tilting the operation lever 46a of the operation instruction portion 46 in the left or right direction.

Note that by tilting the operation lever 46a of the operation instruction portion 46 in one of four regions divided by the forward and backward direction (the direction from the index "Advance" to the index "Retract") and by the right and left direction (the direction from the index "Open" to the index "Close"), the surgeon is capable of simultaneously performing operations of various patterns by combining the operation for leading the treatment portion 51 of the treatment instrument 50 into or out of the distal end portion 11a of the insertion portion 11 of the endoscope 10 with the operation for opening or closing the treatment portion 51 of the treatment instrument 50.

As one example of the operation patterns, for example, as shown in FIG. 10, when the operation lever 46a of the operation instruction portion 46 is tilted in the region between the index "Advance" and the index "Open", the treatment portion 51 of the treatment instrument 50 is led out to the lesion 57, and the treatment portion 51 is opened. Then, as shown in FIG. 11, when the operation lever 46a of the operation instruction portion 46 is tilted in the region between the index "Advance" and the index "Close", the treatment portion 51 of the treatment instrument 50 continues to be led out to the lesion 57, and the treatment portion 51 is closed so as to collect the tissue of the lesion 57.

Further, it is possible to change the advancing and retracting speed of the sheath 52 of the treatment instrument 50 and to change the opening and closing speed of the treatment portion 51 of the treatment instrument 50 depending on the tilting angle at which the operation lever 46a of the operation instruction portion 46 is operated. That is, the each speed is increased according to the magnitude of the angle (angle operated from the initial position) at which the operation lever 46a is tilted.

On the other hand, as shown in FIG. 12, when the rotation operation lever 47a is rotated with respect to the operation lever supporting portion 47b so as to be tilted in the forward or backward direction along the axis of the operation instruction apparatus 45, the rotation instruction portion 47 rotates the sheath 52 of the treatment instrument 50 together with the treatment portion 51. For example, the rotation instruction portion 47 is set such that when the rotation operation lever 47a is tilted to the forward side, the sheath 52 is rotated counterclockwise together with the treatment portion 51 in the case where the distal end is seen from the proximal end, and that when the rotation operation lever 47a is tilted to the backward side, the sheath 52 is rotated clockwise together with the treatment portion 51 in the case where the distal end is seen from the proximal end.

That is, by operating the operation instruction portion 46 with the thumb, or the like, as described above, while grasping the operation instruction apparatus 45 together with the insertion portion 11, the surgeon is capable of advancing or retracting the sheath 52 of the treatment instrument 50 or capable of opening or closing the treatment portion 51. At the same time, by operating the rotation instruction portion 47 with the index finger, or the like, the surgeon is also capable of rotating the treatment portion 51 about the axis of the sheath 52.

More particularly, when the rotation operation lever 47a of the rotation instruction portion 47 is tilted forward or backward, the corresponding instruction signal is supplied to the control apparatus 20 via the signal cable 45a. Then, when receiving the instruction signal, the control apparatus 20 supplies the electric power for rotation in the predetermined direction to the rotating motor 38 via the electrical cable 38a. When receiving the electric power, the rotating motor 38 rotates the gear 39 in the predetermined direction, so as to thereby rotate the sheath 52 of the treatment instrument 50 inserted in the treatment instrument channel of the endoscope 10 about the axis of the sheath 52 via the gear 53a which is in mesh with the gear 39. Note that the predetermined direction in which the gear 39 is rotated is opposite to the direction in which the gear 53a is rotated, and hence the direction of rotation of the motor 38a is opposite to the direction in which the sheath 52 is rotated.

Then, the rotating force of the sheath 52 is transmitted to the treatment portion 51 arranged at distal end, so that the treatment portion 51 is rotated in the predetermined direction. Here, when the rotation operation lever 47a is tilted forward, the treatment portion 51 is rotated in the counter clockwise direction in the case where the distal end is seen from the proximal end, while when the rotation operation lever 47a is tilted backward, the treatment portion 51 is rotated in the clockwise direction in the case where the distal end is seen from the proximal end. Note that the direction of rotation of the sheath 52 and the treatment portion 51 with respect to the direction in which the rotation operation lever 47a is tilted, may also be set opposite to the above described direction.

Further, here, the rotation speed of the sheath 52 and the treatment portion 51 of the treatment instrument 50 can also be changed by the tilting angle to which the rotation operation lever 47a of the rotation instruction portion 47 is operated. That is, the rotation speed is increased according to the magnitude of the tilting angle (angle operated from the initial position) of the operation lever 47a.

As described above, the endoscope system 1 according to the present embodiment is configured such that various operations of the treatment instrument 50 can be performed by the operation instruction apparatus 45 externally inserted onto the insertion portion 11, while the insertion portion 11 is grasped so that the distal end portion 11a of the insertion portion 11 of the endoscope 10, which is inserted into the body cavity of the subject, is surely positioned in the vicinity of the lesion (57). That is, even when the flexible insertion portion 11 of the endoscope 10 receives the peristaltic motion of the body cavity, or the like, the surgeon is capable of performing the various operations of the treatment instrument 50 without releasing the hand from the insertion portion 11. Thus, the surgeon is capable of surely and easily performing medical treatment, or the like, by the treatment instrument 50 without losing the sight of the lesion (57) on the endoscopic image. As a result, the treatment time can be significantly reduced. Further, the surgeon is capable of easily operating the operation instruction portion 46, even while grasping the operation instruction apparatus 45 together with the insertion portion 11 of the endoscope 10 and performing the twisting operation which is unique to the medical endoscope 10.

Further, in the endoscope system 1, various operations of the treatment instrument 50 can be performed at hand even when another type of medical apparatus, such as a type using a high frequency, is used together, and hence the operability of the various switches, which has been complicated and difficult, can be improved. Further, in the endoscope system 1, in the state where the insertion portion 11 is held by the one hand together with the operation instruction apparatus 45, and where the operation portion 12 of the endoscope 10 is held by the other hand, it is possible, at the same time, to operate the bending knobs 15a and 15b which are provided in the main operation portion 12c for performing the bending operation of the bending portion 11b, and to operate the plurality of switches 14 which are provided in the main operation portion 12c for performing the air supply and water supply operation, the suction operation, and for performing the operations of various optical systems, such as the image pickup means and the illumination means which are provided in the distal end portion 11a. Thus, the operability of the various functions provided in the endoscope 10 is not impaired.

Further, the endoscope system 1 can be configured so as to correspond to the treatment instrument 50 rotatable about the axis of the sheath 52. Further, the endoscope system 1 is configured such that in the operation instruction apparatus 45, the rotation instruction portion 47 is provided in the outer peripheral portion opposite to the side on which the operation instruction portion 46 is provided. Thereby, the surgeon is capable of easily simultaneously operating the respective instruction portions 46 and 47 only by the single hand, even when grasping the respective instruction portions 46 and 47 together with the insertion portion 11.

As a result, with the endoscope system 1 according to the present embodiment, while holding the insertion portion 11 to allow the distal end portion 11a of the endoscope 10 to be held at a desired position in the body cavity, the surgeon is capable of easily operating the various functions which are provided in the treatment instrument 50 used together with the endoscope 10, and which are provided in the endoscope 10.

Note that the surgeon may selectively perform the operations in such a manner that the operations, which are frequently performed by the operation instruction portion 46 for advancing or retracting the sheath 52 of the treatment instrument 50 and for opening or closing the treatment portion 51, are performed by the right hand, and that the operations, which are relatively infrequently performed by the operation instruction portion 47 for rotating the treatment portion 51 of the treatment instrument 50, and the various operations (the bending operation, and the air supply and water supply operation) of the endoscope 10, are performed by the left hand.

Further, the treatment instrument 50 according to the present embodiment which configures the endoscope system 1, has a feature in the configuration of the sheath 52. Next, the configuration of the sheath 52 of the treatment instrument 50 will be described in more detail with reference to FIG. 13 to FIG. 15.

As shown in FIG. 13, the sheath 52 of the treatment instrument 50 has two holes 60 as frictional resistance increasing unit in the outer peripheral portion side over the overall length. The holes 60 have a substantially semicircular hole face and are arranged at the positions which are point symmetrical to the center of the sheath 52 so that the circular arc side is set to the outer peripheral side of the sheath 52. Note that reference numeral 58 in the figure denotes the operation wire which is used to operate the treatment portion 51 of the treatment instrument 50 by being pulled and slackened.

In the treatment instrument 50 having the sheath 52 in which the two holes 60 are provided in this way, when the sheath 52 is passed between the two rollers 43a and 43b in the motor-driven treatment instrument advance/retract apparatus 40, the each hole 60 is crushed by the roller surfaces of the respective rollers 43a and 43b. That is, the outer diameter of the sheath 52 is set larger than the distance between the roller surfaces of the respective rollers 43a and 43b.

Specifically, as shown in FIG. 15, the sheath 52 of the treatment instrument 50 is pressed by the respective rollers 43a and 43b, so that the circular arc side of the each hole 60 is crushed. Thereby, the outer peripheral surface of the sheath 52 in press contact with the roller surfaces of the respective rollers 43a and 43b is flattened.

As a result, the contact area of the outer peripheral surface of the sheath 52 in press contact with the roller surfaces of the respective rollers 43a and 43b is increased, so that sufficient frictional force is generated. Thereby, the operation of leading the sheath 52 into and out of the insertion portion 11 of the endoscope 10 is surely performed by the respective rollers 43a and 43b.

As a result, the endoscope system 1 according to the present embodiment is capable of reducing the slip between the respective rollers 43a and 43b arranged in the motor-driven treatment instrument advance/retract apparatus 40, and the sheath 52 of the treatment instrument 50, and is also capable of smoothly advancing or retracting the sheath 52 of the treatment instrument 50 with an excellent response characteristic and without applying an excessive load to the respective rollers 43a and 43b and the sheath 52.

Note that, as shown in FIG. 16, on the sheath 52 of the treatment instrument 50, there may also be formed two flat contact surfaces 61 by flattening the outer peripheral portions which are brought into contact with the roller surfaces of the respective rollers 43a and 43b. That is, as shown in FIG. 17, the respective flat contact surfaces 61 of the sheath 52 are press contacted with the roller surfaces of the respectively contacting rollers 43a and 43b, so that the contact area is increased to generate sufficient frictional force as described above. Thereby, the operation of leading the sheath 52 into and out of the insertion portion 11 of the endoscope 10 is surely performed by the respective rollers 43a and 43b.

In this way, by providing the flat contact surface 61 on the sheath 52, the above described effects can be obtained, and at the same time, the surgeon is capable of specifying the direction around the axis in which the treatment instrument 50 is mounted to the motor-driven treatment instrument advance/retract apparatus 40, in correspondence with the arrangement in which the flat contact surface 61 is surely brought into contact with the respective rollers 43a and 43b.

Further, the sheath 52 of the treatment instrument 50, which has the two holes 60 as described above, may have an index for specifying the position of each hole 60 on the outer peripheral surface.

As the index, for example, a linear index portion 62 as shown in FIG. 18 or an index portion 63 indicating the insertion length of the treatment instrument 50 as shown in FIG. 19 is printed on the outer peripheral surface at the position where the hole 60 of the sheath 52 is provided. The treatment instrument 50 having the sheath 52 provided with the index portions 62 and 63 enables the surgeon to easily confirm the position of the hole 60, and to easily specify the arrangement for allowing the outer peripheral portion of the sheath 52, in which the hole 60 is provided, to be mounted between the respective rollers 43a and 43b at the time when the sheath 52 is mounted to the motor-driven treatment instrument advance/retract apparatus 40. Further, the index portion 63 of the sheath 52, is configured to indicate the length from the treatment portion 51, so that the insertion amount of the treatment instrument 50 can be found at a glance.

Further, as shown in FIG. 20, the outer peripheral surface of the position at which the each hole 60 of the sheath 52 is provided may also be flattened and roughened so that the flattened and roughened surface may also be used an index portion 64. Note that the index portion 64 may only be roughened without being flattened.

Thereby, the friction coefficient between the sheath 52 and the roller surfaces of the respective rollers 43a and 43b is increased, so that the response characteristic of the treatment instrument 50 is more surely improved and the advancing and retracting operation of leading into or out of the insertion portion 11 of the endoscope 10 is improved.

Further, when one of the index portions 61 to 64 is provided on the sheath 52, the surgeon is capable of easily mounting the treatment instrument 50 to the motor-driven treatment instrument advance/retract apparatus 40, and thereby the mounting time can also be reduced.

Second Embodiment

Next, a second embodiment according to the present invention will be described with reference to FIG. 21 and FIG. 22.

Figure 21:
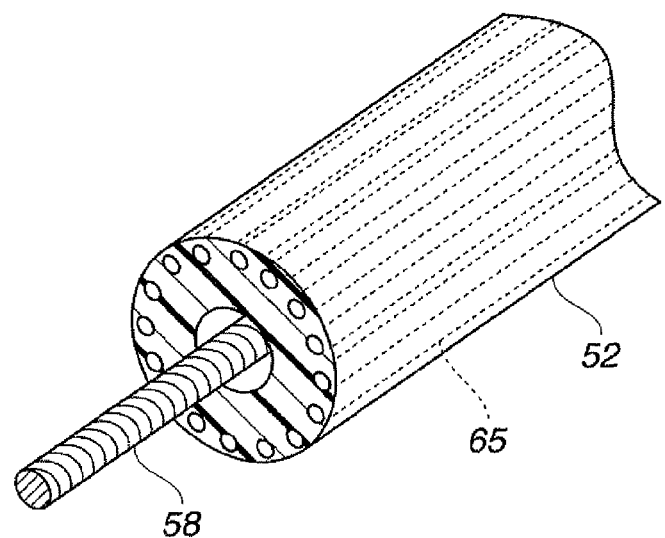
FIG. 21 is a perspective view showing, partially in cross section, a treatment instrument sheath according to a second embodiment.
Figure 22:
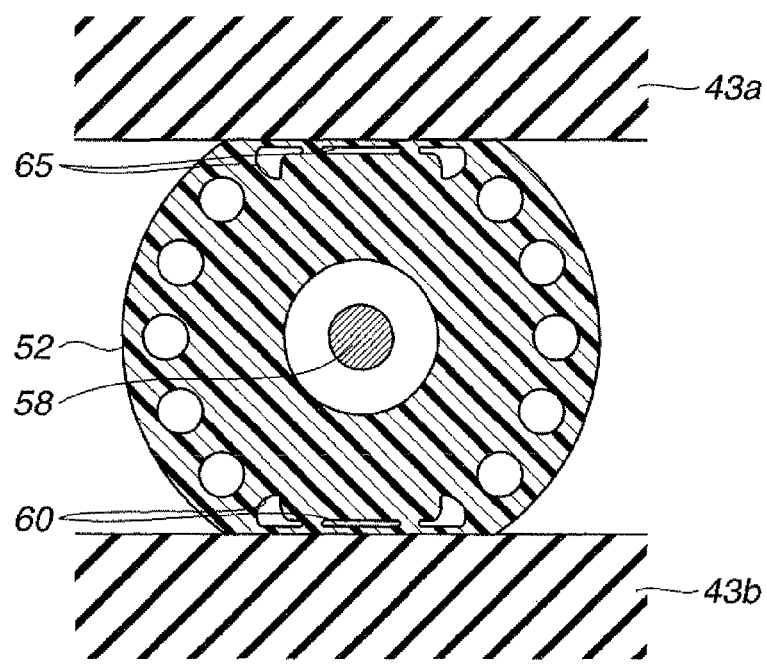
FIG. 22 is a sectional view showing the sheath in a state where the sheath is inserted between respective rollers of the motor-driven treatment instrument advance/retract apparatus, according to the second embodiment.

FIG. 21 and FIG. 22 relate to the second embodiment. FIG. 21 is a perspective view showing, partially in cross section, a treatment instrument sheath. FIG. 22 is a sectional view showing the sheath in a state where the sheath is inserted between rollers. Note that in the description of the present embodiment, components the same as those of the first embodiment are denoted by the same reference numerals and characters, and their description is omitted.

As shown in FIG. 21, in the sheath 52 of the treatment instrument 50 according to the present embodiment, a plurality of holes 65 serving as frictional resistance increasing unit are provided along the longitudinal direction in the inside and along the vicinity of the outer periphery of the sheath. In the sheath 52 having the plurality of holes 65 formed in this way, the outer peripheral portion pressed by the roller surfaces of the respective rollers 43a and 43b of the motor-driven treatment instrument advance/retract apparatus 40 is flattened, as shown in FIG. 22, in such a way that some of the holes 65 are crushed by the respective roller surfaces.

Therefore, the endoscope system 1 having the treatment instrument 50 according to the present embodiment makes it possible to obtain the effect of the first embodiment, and has a feature that the sheath 52 of the treatment instrument 50 is flattened in any part of the entire periphery around the axis of the sheath 52 by being pressed by the respective rollers 43a and 43b.

That is, it is possible to secure the contact area between the outer peripheral surface of the sheath 52 and the each roller surface in any direction. Therefore, it is possible for the surgeon to mount the treatment instrument 50 to the motor-driven treatment instrument advance/retract apparatus 40 in any direction about the axis of the sheath 52.

As a result, according to the endoscope system 1 of the present embodiment, in addition to the effect of the first embodiment, it is possible for the surgeon to easily mount the treatment instrument 50 to the motor-driven treatment instrument advance/retract apparatus 40.

Third Embodiment

Next, a third embodiment according to the present invention will be described with reference to FIG. 23 to FIG. 26.

Figure 23:
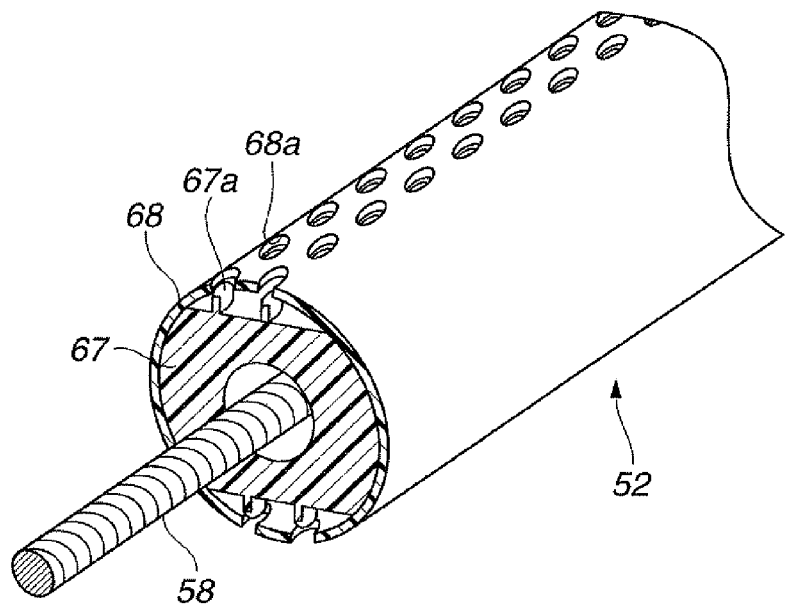
FIG. 23 is a perspective view showing, partially in cross section, a treatment instrument sheath according to a third embodiment.
Figure 24:
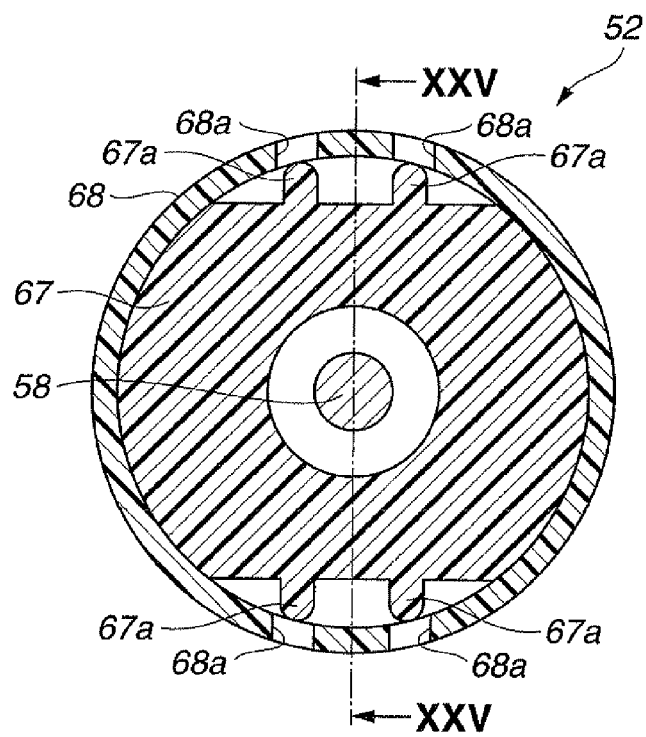
FIG. 24 is a longitudinal sectional view showing the treatment instrument sheath, according to the third embodiment.
Figure 25:
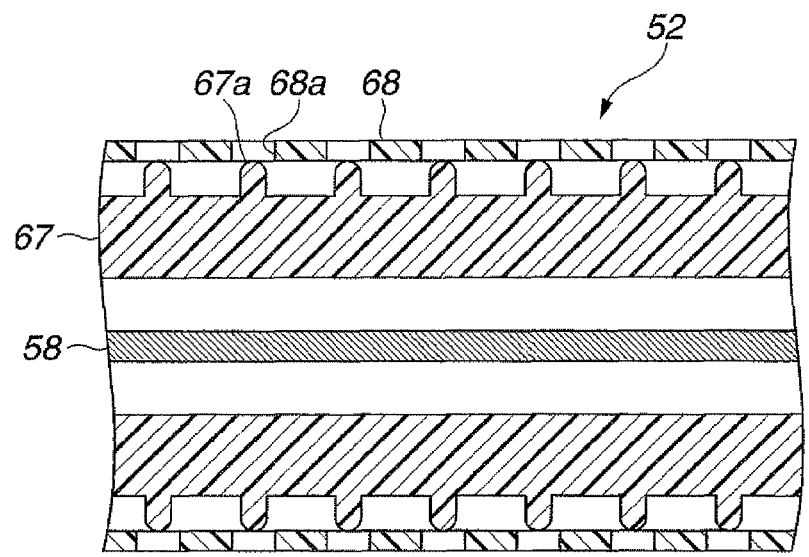
FIG. 25 is a lateral sectional view showing the treatment instrument sheath, according to the third embodiment.
Figure 26:
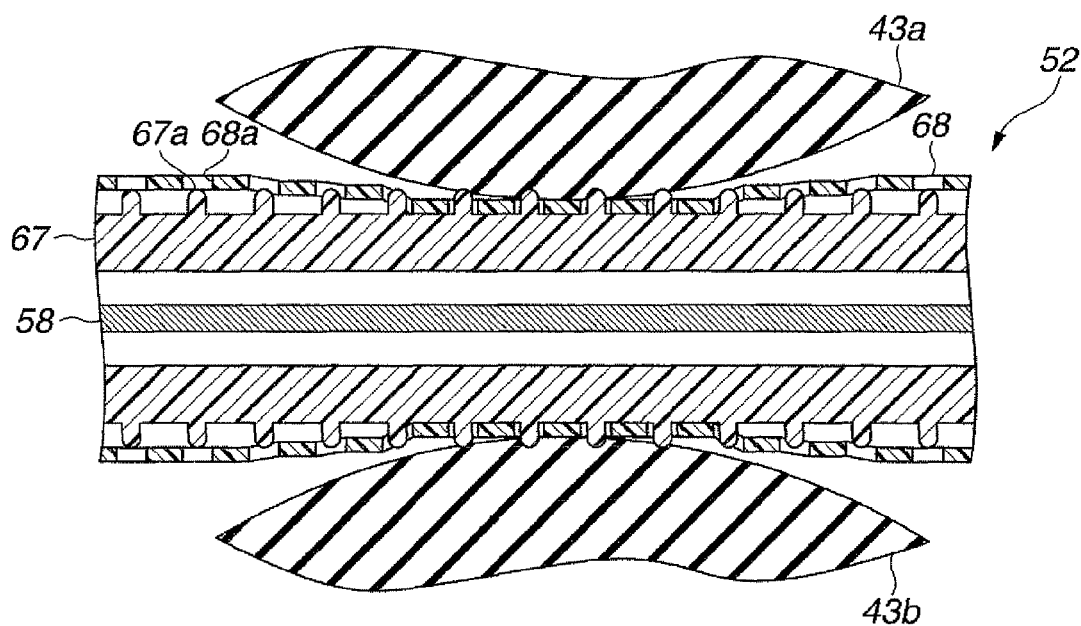
FIG. 26 is a sectional view showing the sheath in a state where the sheath is inserted between respective rollers of the motor-driven treatment instrument advance/retract apparatus, according to the third embodiment.

FIG. 23 to FIG. 26 relate to the third embodiment. FIG. 23 is a perspective view showing, partially in cross section, a treatment instrument sheath. FIG. 24 is a sectional view showing the sheath of the treatment instrument. FIG. 25 is a sectional view of the sheath of the treatment instrument along the line XXV-XXV in FIG. 24. FIG. 26 is a sectional view showing the sheath in a state where the sheath is inserted between respective rollers of a motor-driven treatment instrument advance/retract apparatus. Note that also in the description according to the present embodiment, the same components as those of the above described respective embodiments are denoted by the same reference numerals and characters, and their description is omitted.

As shown in FIG. 23, the sheath 52 of the treatment instrument 50 according to the present embodiment is configured by a tubular sheath main body 67 which is formed of synthetic resin and in which the operation wire 58 is inserted, and a covering tube 68 which is formed of synthetic resin and covers the outer periphery of the sheath main body 67.

As shown in FIG. 24 and FIG. 25, in the sheath main body 67 of the sheath 52, two outer peripheral portions in the upper and lower direction when viewed toward the paper surface are flattened, and a plurality of projecting portions 67a serving as frictional resistance increasing unit are provided to project from the respective flattened surfaces so as to form two rows along the axial direction.

The outer diameter of the covering tube 68 is set to be larger than the distance between the separated roller surfaces of the respective rollers 43a and 43b of the motor-driven treatment instrument advance/retract apparatus 40. Further, a plurality of holes 68a are bored in the covering tube 68 in two rows along the axial direction in correspondence with the positions of the respective projecting portions 67a of the sheath main body 67. Note that the holes 68a have a hole diameter slightly larger than the diameter of the projecting portion 67a. Note that the projecting portions 67a and the holes 68a are not limited to be arranged in two rows, but may also be arranged in one row or in more than two rows.

In the endoscope system 1 according to the present embodiment configured in this way, when the sheath 52 of the treatment instrument 50 is passed between the respective rollers 43a and 43b of the motor-driven treatment instrument advance/retract apparatus 40 as shown in FIG. 26, the covering tube 68 is crushed by being pressed by the respective rollers 43a and 43b. At this time, the covering tube 68 is pushed to the side of the sheath main body 67, and hence the plurality of projecting portions 67a of the sheath main body 67 are made to penetrate the respective holes 68a of the covering tube 68, so as to project from the surface of the sheath 52.

Thereby, the friction between the respective roller surfaces and the projecting portions 67a projected from the surface of the sheath 52 is increased, so that the respective rollers 43a and 43b are gripped.

As a result, according to the endoscope system 1 of the present embodiment, in the advancing and retracting operation of the treatment instrument 50, the respective rollers are surely rotated, and thereby the excellent response characteristic in the advancing and retracting operation is obtained. Therefore, it is possible to improve the advancing and retracting operation of leading the treatment instrument 50 into and out of the insertion portion 11 of the endoscope 10.

Further, the respective holes 68a of the covering tube 68, which are provided on the surface of the sheath 52, serve as the index, so as to enable the surgeon to specify the arrangement position of the projecting portion 67a. Thereby, the surgeon is capable of easily performing arrangement for mounting the sheath 52 between the respective rollers 43a and 43b at the time of mounting the treatment instrument 50 to the motor-driven treatment instrument advance/retract apparatus 40.

Figure 27:
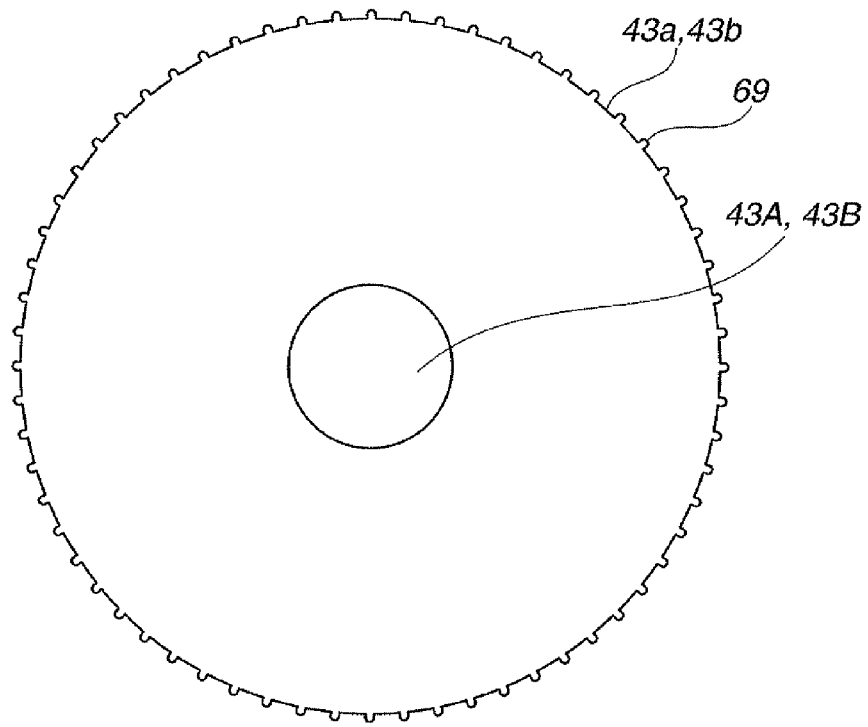
FIG. 27 is a plan view showing a roller as a modification, according to the third embodiment.

Note that as shown in FIG. 27, a plurality of projecting portions 69 may be provided on the surface of the respective rollers 43a and 43b of the motor-driven treatment instrument advance/retract apparatus 40.

Figure 28:
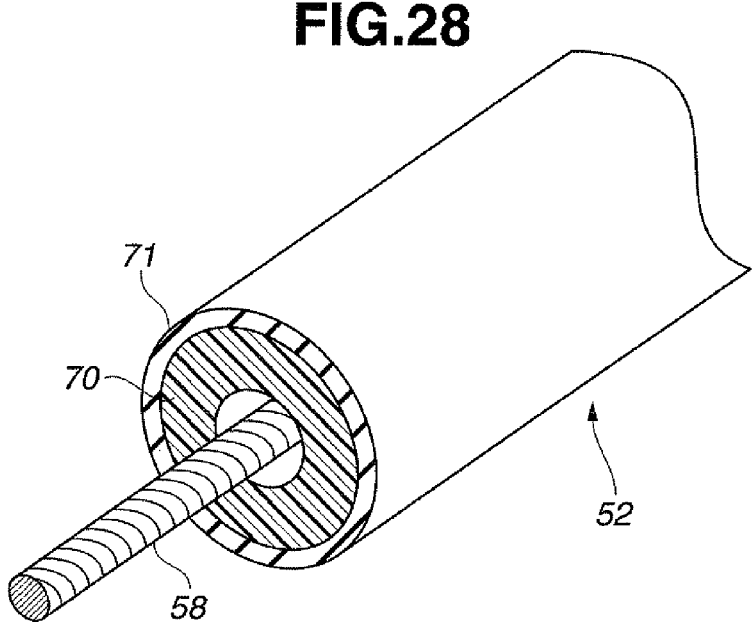
FIG. 28 is a perspective view showing, partially in cross section, a treatment instrument sheath in correspondence with FIG. 27, according to the modification of the third embodiment.

Further, as shown in FIG. 28, in correspondence with the respective rollers 43a and 43b having the plurality of projecting portions 69, the sheath 52 of the treatment instrument 50 is configured as a two layer tube having a tube main body 70 and a covering tube body 71 which is formed of an elastic member, or the like, and is provided in the outer peripheral portion of the tube main body 70.

The sheath 52 of the treatment instrument 50, which is configured in this way and is inserted between the respective rollers 43a and 43b, is capable of having the same effects as those as described above, because the plurality of projecting portions 69 of the respective rollers 43a and 43b are made to bite into the covering tube body 71.

Figure 29:
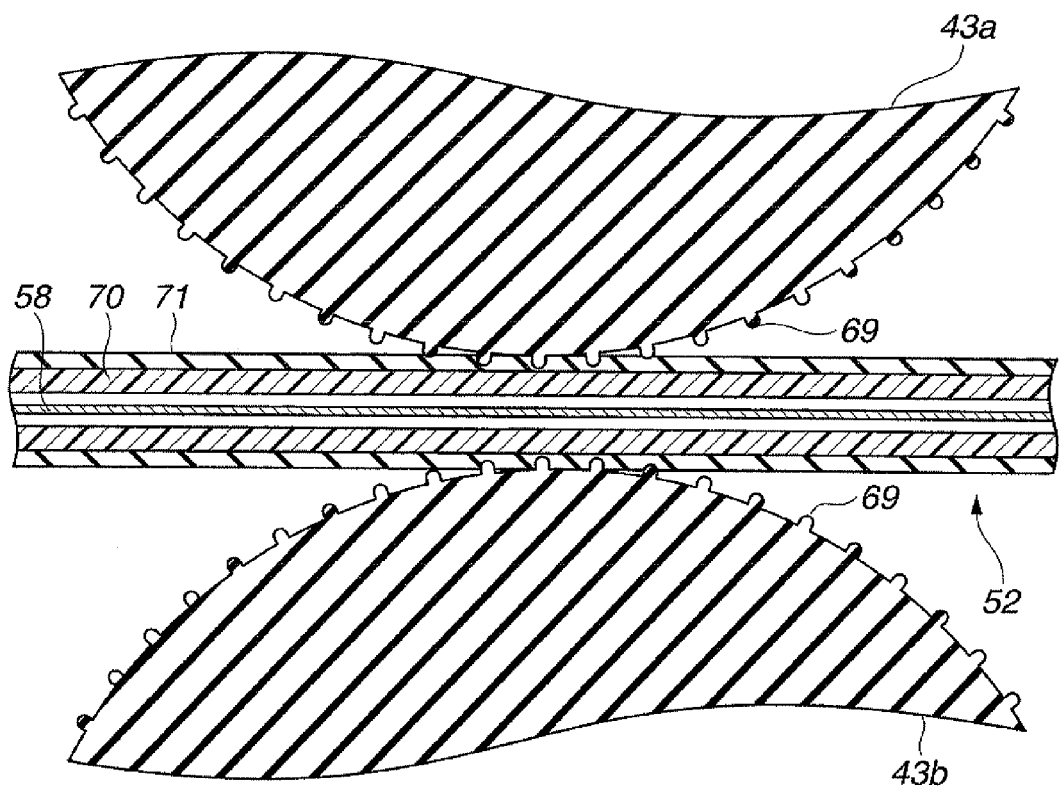
FIG. 29 is a sectional view showing the sheath in a state where the sheath is inserted between the respective rollers of the motor-driven treatment instrument advance/retract apparatus, according to the modification of the third embodiment.

Note that FIG. 27 is a plan view showing a roller as a modification, FIG. 28 is a perspective view showing, partially in cross section, the sheath of the treatment instrument in correspondence with FIG. 27, and FIG. 29 is a sectional view showing the sheath in the state where the sheath is inserted between the respective rollers of the motor-driven treatment instrument advance/retract apparatus.

The present invention described in the above embodiments is not limited to the above described embodiments, and various modifications are possible in an implementation stage within the scope and spirit of the present invention. Further, various stages of the present invention are included in the above described embodiments, and various inventions may be extracted by properly combining the plurality of disclosed constitution elements.

For example, even when several constitution elements are eliminated from all the constitution elements as shown in the embodiments, if it is possible to solve the above described problem and an effect as described as the effect of the present invention is obtained, the configuration in which the constitution elements are eliminated may also be extracted as the present invention.

What is claimed is:

1. An endoscope system comprising:
an endoscope including an elongated insertion portion;
a medical instrument configured to be inserted in a channel of the insertion portion of the endoscope and to include an elongated flexible sheath; and
an advancing and retracting apparatus configured to advance and retract the sheath of the medical instrument in the channel with two rollers,
wherein the sheath of the medical instrument has an outer diameter larger than a distance between roller surfaces of the two rollers and includes:
a frictional resistance increasing unit including a plurality of holes formed in a vicinity of an outer peripheral surface of the sheath, wherein the frictional resistance increasing unit is configured to be pressed by the two rollers and crushed by the respective roller surfaces such that the outer peripheral surface of the sheath is flattened.

2. The endoscope system according to claim 1, wherein the plurality of holes are two holes respectively arranged at positions which are point symmetrical to a center of the sheath.

3. The endoscope system according to claim 2, wherein the sheath further includes, on outer peripheral surfaces at positions where the two holes are provided, index portions for specifying the positions of the two holes.

4. The endoscope system according to claim 2, wherein the sheath further includes roughened outer peripheral surfaces at positions where the two holes are provided.

5. The endoscope system according to claim 3, wherein the sheath further includes roughened outer peripheral surfaces at positions where the two holes are provided.

6. The endoscope system according to claim 1, wherein:
the sheath further includes a tube main body and a covering tube, together forming a two layer tube,
the plurality of holes formed in the vicinity of the outer peripheral surface of the sheath is formed between an outer peripheral surface of the tube main body and an inner peripheral surface of the covering tube, and
the frictional resistance increasing unit further includes a plurality of projecting portions which are formed on the tube main body, and which are made to project on the outer surface of the sheath from a plurality of holes formed in the covering tube, toward the respective roller surfaces of the two rollers in the state where the sheath is inserted between the two rollers.

7. A medical instrument which is inserted into a channel of an insertion portion of an endoscope and which is advanced and retracted in the channel by an advancing and retracting apparatus having two rollers, the medical instrument comprising:
a treatment portion which is led out from a distal end of the insertion portion and which is configured to perform various treatment operations in a body cavity; and
an elongated flexible sheath to the distal end side of which the treatment portion is continuously connected,
wherein the sheath is configured to have an outer diameter larger than a distance between roller surfaces of the two rollers, and includes:
a frictional resistance increasing unit including a plurality of holes formed in a vicinity of an outer peripheral surface of the sheath, wherein the frictional resistance increasing unit is configured to be pressed by the two rollers and crushed by the respective roller surfaces such that the outer peripheral surface of the sheath is flattened.

8. The medical instrument according to claim 7, wherein the plurality of holes are two holes respectively arranged at positions which are point symmetrical to a center of the sheath.

9. The medical instrument according to claim 8, wherein the sheath further includes, on outer peripheral surface at positions where the two holes are provided, index portions for specifying the positions of the two holes.

10. The medical instrument according to claim 8, wherein the sheath further includes roughened outer peripheral surfaces at the positions where the two holes are provided.

11. The medical instrument according to claim 9, wherein the sheath further includes roughened outer peripheral surfaces at the positions where the two holes are provided.

12. The medical instrument according to claim 7, wherein:
the sheath further includes a tube main body and a covering tube, together forming a two layer tube,
the plurality of holes formed in the vicinity of the outer peripheral surface of the sheath is formed between an outer peripheral surface of the tube main body and an inner peripheral surface of the covering tube, and
the frictional resistance increasing unit further includes a plurality of projecting portions which are formed on the tube main body, and which are made to project on the outer surface of the sheath from a plurality of holes formed in the covering tube, toward the respective roller surfaces of the two rollers in the state where the sheath is inserted between the two rollers.

13. The endoscope system according to claim 1, wherein each of the plurality of holes has a substantially semicircular hole face and is arranged such that a circular arc side of the substantially semicircular hole face is set to an outer peripheral side of the sheath.

14. The endoscope system according to claim 7, wherein each of the plurality of holes has a substantially semicircular hole face and is arranged such that a circular arc side of the substantially semicircular hole face is set to an outer peripheral side of the sheath.

* * * * *